(12) United States Patent
Hashimoto et al.

(10) Patent No.: US 8,460,276 B2
(45) Date of Patent: Jun. 11, 2013

(54) MANIPULATION MECHANISM AND MEDICAL DEVICE INSTRUMENT

(75) Inventors: Tatsutoshi Hashimoto, Tokyo (JP); Takumi Dejima, Tokyo (JP)

(73) Assignee: Olympus Medical Systems Corp. (JP)

( * ) Notice: Subject to any disclaimer, the term of this patent is extended or adjusted under 35 U.S.C. 154(b) by 863 days.

(21) Appl. No.: 12/551,618

(22) Filed: Sep. 1, 2009

(65) Prior Publication Data

US 2010/0063354 A1    Mar. 11, 2010

Related U.S. Application Data

(60) Provisional application No. 61/093,492, filed on Sep. 2, 2008.

(51) Int. Cl.
*A61B 17/00* (2006.01)
(52) U.S. Cl.
USPC .............................................. 606/1
(58) Field of Classification Search
USPC ............. 606/1; 604/528, 264, 523; 600/106
See application file for complete search history.

(56) References Cited

U.S. PATENT DOCUMENTS

| | | | |
|---|---|---|---|
| 5,472,017 A | 12/1995 | Kovalcheck | |
| 2005/0065397 A1 | 3/2005 | Saadat et al. | |
| 2007/0225641 A1* | 9/2007 | Schneider et al. | 604/93.01 |
| 2007/0299387 A1* | 12/2007 | Williams et al. | 604/22 |

FOREIGN PATENT DOCUMENTS

| JP | 2007-030145 | 2/2007 |
|---|---|---|
| JP | 2007-097620 | 4/2007 |

OTHER PUBLICATIONS

Extended European Search Report dated Feb. 3, 2010 in corresponding European Patent Application No. 09011208 (English language).

* cited by examiner

*Primary Examiner* — Bill Thomson
*Assistant Examiner* — Sebastian X Lukjan
(74) *Attorney, Agent, or Firm* — Ostrolenk Faber LLP

(57) ABSTRACT

A manipulation mechanism for moving an oscillating body in a soft endoscope in a stable locus such as for laparoscopic procedures. The mechanism has first and second oscillating portions oscillating on first and second imaginary planes and guide members which regulate oscillating locus of the first and second oscillating portions. A manipulation stick is fixed to the second oscillating portion and capable of moving on the second imaginary plane. The oscillating portions respectively have a force-transmitting-member attachment member, a pair of first support members, and a force receiving member. The pair of first support members is provided with first and second convex portions and each of the first and second guide members is provided with first and second groove portions formed so as to be closer to each other in a direction away from the manipulation reference plane.

16 Claims, 25 Drawing Sheets

FIG. 29

| | LEFT TREATMENT TOOL | RIGHT TREATMENT TOOL |
|---|---|---|
| PATTERN A | ARM MECHANISM WITH SECOND CURVE | ARM MECHANISM WITH SECOND CURVE |
| PATTERN B | ARM MECHANISM WITHOUT SECOND CURVE | ARM MECHANISM WITHOUT SECOND CURVE |
| PATTERN C | COMMON TREATMENT TOOL OR CLAMP RASING STAND | ARM MECHANISM WITH SECOND CURVE |
| PATTERN D | COMMON TREATMENT TOOL OR CLAMP RASING STAND | ARM MECHANISM WITHOUT SECOND CURVE |

FIG. 30

| | LEFT AND RIGHT TREATMENT TOOLS | EXISTENCE AND THE LIKE OF ASSISTANT |
|---|---|---|
| PATTERN A | CASE WHERE LEFT AND RIGHT ARMS ARE ARM MECHANISMS | SURGEON PERFORMS OPERATIONS OF RECIPROCATING, OPENING/CLOSING, AND ROTATING TREATMENT TOOL. |
| PATTERN B | | CASE WITHOUT ASSISTANT. SURGEON PERFORMS OPERATIONS OF RECIPROCATING, OPENING/CLOSING, AND ROTATING ARM MECHANISM AND CLAMP. |
| PATTERN C | CASE WHERE ONE IS ARM MECHANISM, THE OTHER IS GENERAL CLAMP, AND TISSUE IS TURNED OVER JUST BY RECIPROCATING CLAMP | CASE WITH ASSISTANT. ASSISTANT PERFORMS OPERATIONS OF OPENING/CLOSING AND ROTATING CLAMP AND SURGEON PERFORMS OPERATION OF RECIPROCATING CLAMP. |
| PATTERN D | | CASE WITH ASSISTANT. ASSISTANT PERFORMS OPERATIONS OF RECIPROCATING, OPENING/CLOSING, AND ROTATING CLAMP. |
| PATTERN E | CASE WHERE ONE IS ARM MECHANISM AND ARM MECHANISM IS BENT BY CLAMP RASING STAND SO AS TO ELEVATE OR PULL TISSUE | CASE WITHOUT ASSISTANT. |
| PATTERN F | | CASE WITH ASSISTANT. ASSISTANT PERFORMS OPERATIONS OF OPENING/CLOSING AND ROTATING TREATMENT TOOL. |
| PATTERN G | | CASE WITH ASSISTANT. ASSISTANT PERFORMS OPERATIONS OF RECIPROCATING, OPENING/CLOSING, AND ROTATING TREATMENT TOOL. |

MANIPULATION MECHANISM AND MEDICAL DEVICE INSTRUMENT

BACKGROUND OF THE INVENTION

1. Field of the Invention

The present invention relates to a manipulation mechanism and a mechanical instrument which is used while being inserted into a body cavity in combination with a soft endoscope.

Priority is claimed on U.S. Provisional Application No. 61/093,492, filed Sep. 2, 2008, the content of which is incorporated herein by reference.

2. Background Art

As a method of performing a medical action such as an observation or a treatment on the internal organs of a human body, there is known a laparoscopic surgery which performs a surgical technique by forming a plurality of openings in an abdominal wall instead of making a large incision, and inserting the medical instruments such as an abdominoscope or a clamp into the respective openings. In such a surgery, since only small openings are formed in the abdominal wall, it is advantageous in that the stress on the patient is reduced.

In addition, as a method of reducing the stress to the patient, a method has been proposed for performing a surgical technique by inserting a soft endoscope through a natural passageway such as patient's mouth, nose, or anus. An example of an endoscope device (medical instrument) used in such a surgical technique is disclosed in US Patent Application Laid-open No. 2005/0065397.

In the disclosed endoscope device, arm portions of which front ends can be bent are respectively inserted through a plurality of lumens disposed in a soft inserting portion inserted through a patient's mouth. When treatment tools are respectively inserted through the arm portions, it is possible to approach the treatment tools to a treatment portion in different directions, and to continuously perform a plurality of surgical techniques in a state in which one endoscope is inserted into a body cavity.

Also, in the arm portion (manipulation mechanism) disclosed in the above-described specification, four pulling wires are disposed along the arm portion so as to be located at the same interval in the circumferential direction. In the pulling wires, the base ends are attached to a steering opening (oscillating body) in the base end of the arm portion, and the front ends are attached to the front end of the arm portion. In addition, it is possible to change a direction of the treatment portion protruding from the front end of the arm portion by curving the front end of the arm portion in such a manner that the base end of the treatment tool communicating with the opening and the arm portion is inclined so as to rotate the opening relative to the arm portion.

However, the method of attaching the opening to the base end of the arm portion is not clearly shown. Additionally, the position of the opening deviates from the base end of the arm portion when the opening is rotated, which may deteriorate the operability of the treatment tool.

SUMMARY OF THE INVENTION

The present invention is contrived in consideration of the above-described problems, and an object of the invention is to provide a manipulation mechanism that an oscillating body moves in a stable locus, and a medical instrument having the manipulation mechanism.

In the present invention, there is provided a manipulation mechanism including: an oscillating body which is disposed on a first imaginary plane, where first and second imaginary planes are parallel to each other with respect to a manipulation reference plane; and a holding body which is disposed on the second imaginary plane so as to regulate an oscillating locus of the oscillating body, wherein the oscillating body is provided with first and second convex portions which are spaced from each other and protrude toward the holding body; the holding body is provided with first and second groove portions which respectively guide the first and second convex portions; and the first and second groove portions are formed to be closer to each other in a direction away from the manipulation reference plane on one side of the manipulation reference plane from a point on the manipulation reference plane as a start point.

BRIEF DESCRIPTION OF THE DRAWINGS

FIG. 29 is a table showing a pattern of a treatment tool of the endoscope device according to the present invention.

FIG. 30 is a table showing patterns obtained by the relationship between a treatment tool of the endoscope device according to the present invention and an existence of an assistant.

DETAILED DESCRIPTION OF THE INVENTION

Hereinafter, embodiments of the present invention will be described. In addition, the basic structure of an endoscope device is disclosed in U.S. patent Ser. No. 11/652,880 which is related to the present invention, and the disclosed contents are incorporated in the following description by reference.

First Embodiment

An endoscope device 1 according to this embodiment is used to perform a treatment inside a comparatively narrow space such as a digestive canal, and one surgeon is capable of manipulating the endoscope device and performing a treatment by using the endoscope device. In addition, for convenience of description, parts of several diagrams are omitted.

Figure 1:
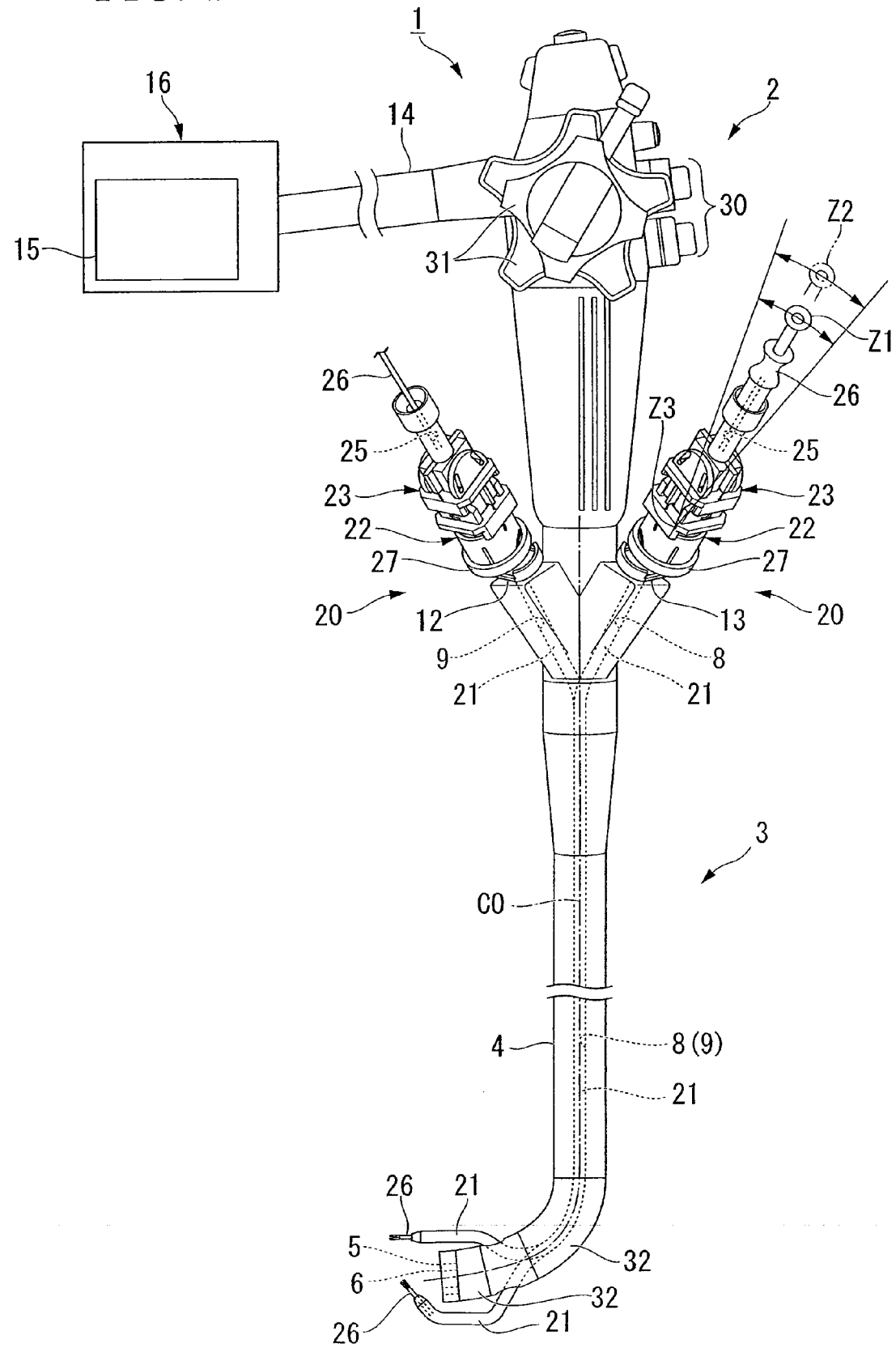
FIG. 1 is an overall view showing an endoscope device according to a first embodiment of the present invention.

As shown in FIG. 1, the endoscope device 1 has a configuration in which a tubular endoscope inserting portion 3 integrally extends from one end of an endoscope manipulating portion 2 and two arm mechanisms (medical instruments) 20 are attached to the one end.

The endoscope inserting portion 3 is elongate and flexible, and the configuration thereof is the same as that disclosed in U.S. patent Ser. No. 11/652,880. That is, the endoscope inserting portion 3 includes a flexible sheath 4 which covers the outer peripheral surface of the endoscope inserting portion 3, an illumination mechanism 5 which applies illumination light in the forward direction, and an observation mechanism 6 which has an imaging element such as a CCD (not shown in the figure) for observing a forward area. In addition, the inside of the endoscope inserting portion 3 is provided with a first lumen (operation channel) 8 and a second lumen (operation channel) 9 which extend from the front end of the endoscope inserting portion 3 to the endoscope manipulating portion 2.

The endoscope manipulating portion 2 includes clamp openings 12 and 13 which respectively communicate with the first and second lumens 8 and 9, and a control mechanism 16 which is connected to the endoscope manipulating portion 2 through a universal cable 14 and which has a monitor 15. The control mechanism 16 has a light source (not shown in the figure) which supplies illumination light to the illumination mechanism 5. In addition, the image observed by the observation mechanism 6 is transmitted to the control mechanism 16 through the universal cable 14, and is displayed on the monitor 15 through an appropriate image process.

In addition, the endoscope manipulating portion 2 further includes a switch 30 and an angle knob 31. The switch 30 is manipulated, for example, upon performing an air supply operation, a water supply operation, and a suction operation through the first lumen 8. The angle knob 31 is used when a third curve 32, described later, of the endoscope inserting portion 3 is bent in four directions with respect to the axis.

Figure 2:
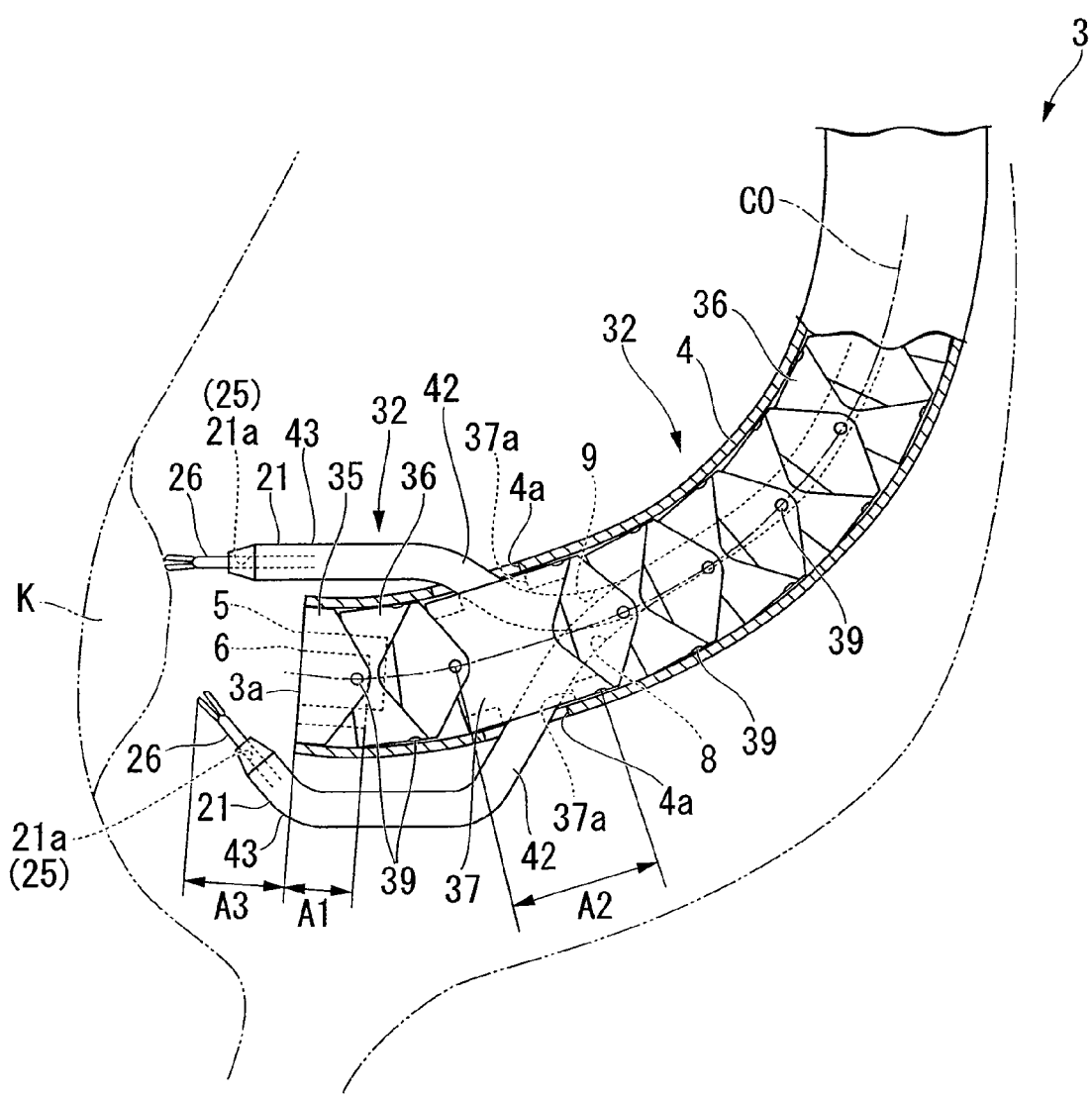
FIG. 2 is an enlarged cut-away view showing a part of a front end of an insertion portion of the endoscope device.

As shown in FIG. 2, in the inside of the endoscope inserting portion 3, in the same manner as the known configuration, a plurality of substantially cylindrical curve pieces 36 is disposed to be connected to each other in a predetermined range along the axis C0 of the endoscope inserting portion 3, and the third curve 32 of the front end of the endoscope inserting portion 3 can be bent with respect to the axis C0.

In the inside of the endoscope inserting portion 3, a first support piece 35 which has the illumination mechanism 5 and the observation mechanism 6 attached to a front end surface thereof and is formed in a cylindrical shape provided with a top, the plurality of curve pieces 36, a second substantially cylindrical support piece 37 which has a pair of openings 37a at opposing side surfaces, and the plurality of curve pieces 36 are disposed in a sequential order from the front end of the endoscope inserting portion 3. In addition, a portion between the first support piece 35 and the curve piece 36, a portion between the second support piece 37 and the curve piece 36, and a portion between the curve pieces 36 are perpendicular to the axis C0 of the endoscope inserting portion 3, and are rotatably connected a plurality of hinges 39 which is differently disposed in a direction seen from the axis C0.

The front ends of four endoscope manipulating wires (not shown in the figure) disposed at the same interval in the circumferential direction are attached to an inner surface of a base end of the first support piece 35, and the endoscope manipulating wires disposed at opposing positions to make a pair. The base ends of two pairs of endoscope manipulating wires are inserted through the inside of the endoscope inserting portion 3 and the endoscope manipulating portion 2, and are respectively fixed to the angle knob 31. Then, when the angle knob 31 is rotated, it is possible to rotate the third curve 32 in four directions with respect to the axis C0.

In the front end of the endoscope inserting portion 3, the first lumen 8 and the second lumen 9 displace from the axis C0 of the endoscope inserting portion 3 so as to respectively communicate with passageways 37a of the second support piece 37.

In this embodiment, in the front end of the endoscope inserting portion 3, the ranges of the lengths A1 and A2 of the first and second support pieces 35 and 37 taken along the axis C0 are the rigid ranges in which the endoscope inserting portion 3 cannot be bent, and the other ranges are the soft ranges in which the endoscope inserting portion 3 can be bent.

As shown in FIG. 1, each of the arm mechanisms 20 includes an arm portion (inserting portion) 21 which is formed in an elongate tubular shape so as to be bent, a body portion 22 which is formed in a shaft shape so as to be connected to the arm portion 21, and an arm manipulating portion (manipulating mechanism) 23 which is attached to the body portion 22 and is used to manipulate the front end of the arm portion 21 to be bent. A treatment tool 26 such as a gripping clamp can be reciprocatingly inserted through a channel 25 which is formed to communicate with the arm portion 21, the body portion 22, and the arm manipulating portion 23. In this embodiment, two arm mechanisms 20, through which the treatment tool 26 is inserted, are used. The first lumen 8, the second lumen 9, and the arm portion 21 are separably and reciprocatingly inserted through each arm mechanism 20, and the bodies 22 are respectively attached to the clamp pieces 12 and 13. In addition, in the inside of the first lumen 8 and the second lumen 9, the arm portion 21 is adapted to be rotatable about the axis thereof.

In order to prevent the movements of the arm manipulating portions 23 from interfering with each other, the arm mechanisms 20 through which the lumens 8 and 9 are inserted are respectively attached to the clamp openings 12 and 13 so that the base ends of the arm mechanisms 20 are distant from each other while forming a predetermined angle with respect to the axis C0 of the endoscope inserting portion 3.

Note that, in this embodiment, the gripping clamp is used as the treatment tool 26, but the present invention is not limited thereto. For example, a high-frequency knife, a snare, or the like may be used as the treatment tool 26.

In the inside of the arm portion 21, in the same manner as the above-described endoscope inserting portion 3, curve pieces (not shown in figure) are disposed to be connected to each other in a predetermined range along the axis of the arm portion 21 in the front end of the arm portion 21.

the front ends of four arm portion manipulating wires (not shown in figure) (first and second manipulation members) disposed at the same interval in the circumferential direction are attached to the inner surface of the base end side of the curve piece disposed at the forefront end of the arm portion 21, and the arm portion manipulating wires disposed at the opposing positions to make a pair. Two pairs of arm portion manipulating wires are respectively inserted through arm portion manipulating sheaths (not shown in figure) disposed and fixed to the inside of the arm portion 21, and the base ends of the arm portion manipulating wires respectively extend to the arm manipulation portions 23 of the arm mechanisms 20. In addition, when the arm portion manipulating wires are pulled, it is possible to bend a first curve (curve portions) 43.

In addition, as shown in FIG. 2, in the arm portion 21, front ends of a pair of second curve manipulating wires (not shown in figure) are attached to an inner surface of a curve piece disposed at a second curve 42 corresponding to a middle portion of the curve pieces connected to each other through a predetermined range. Each second curve manipulating wires is inserted through a second curve manipulating sheath (not shown) disposed and fixed to the inside of the arm portion 21, and the base end of the second curve manipulating wire extends to the body portion 22 of the arm mechanism 20.

In addition, the arm portions 21 are respectively inserted through passageways 4a formed in the sheath 4 and the lumens 8 and 9, and protrude forward from the front end surface 3a of the endoscope inserting portion 3.

Figure 3:
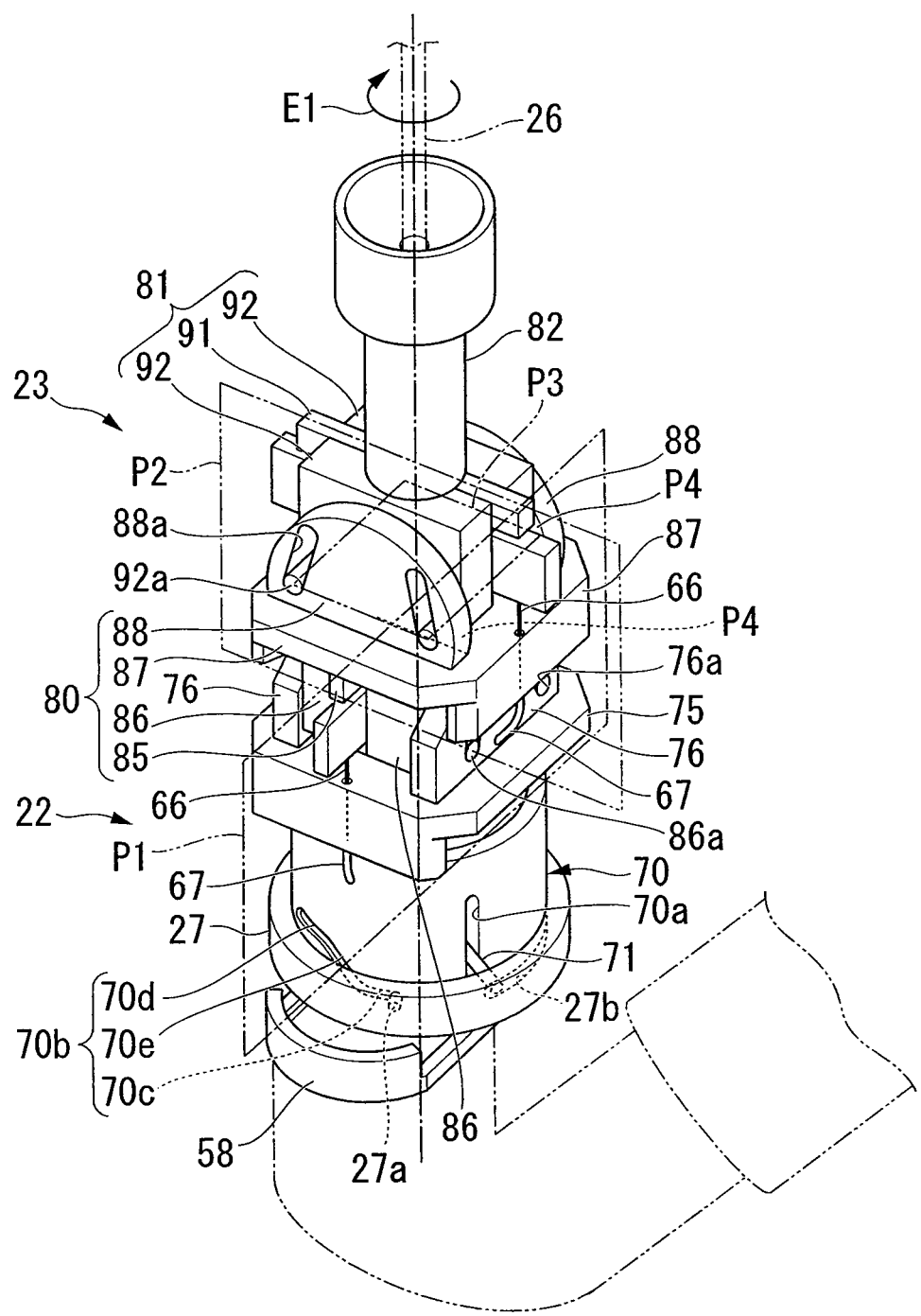
FIG. 3 is a perspective view showing a main part of an arm mechanism of the endoscope device.
Figure 4:
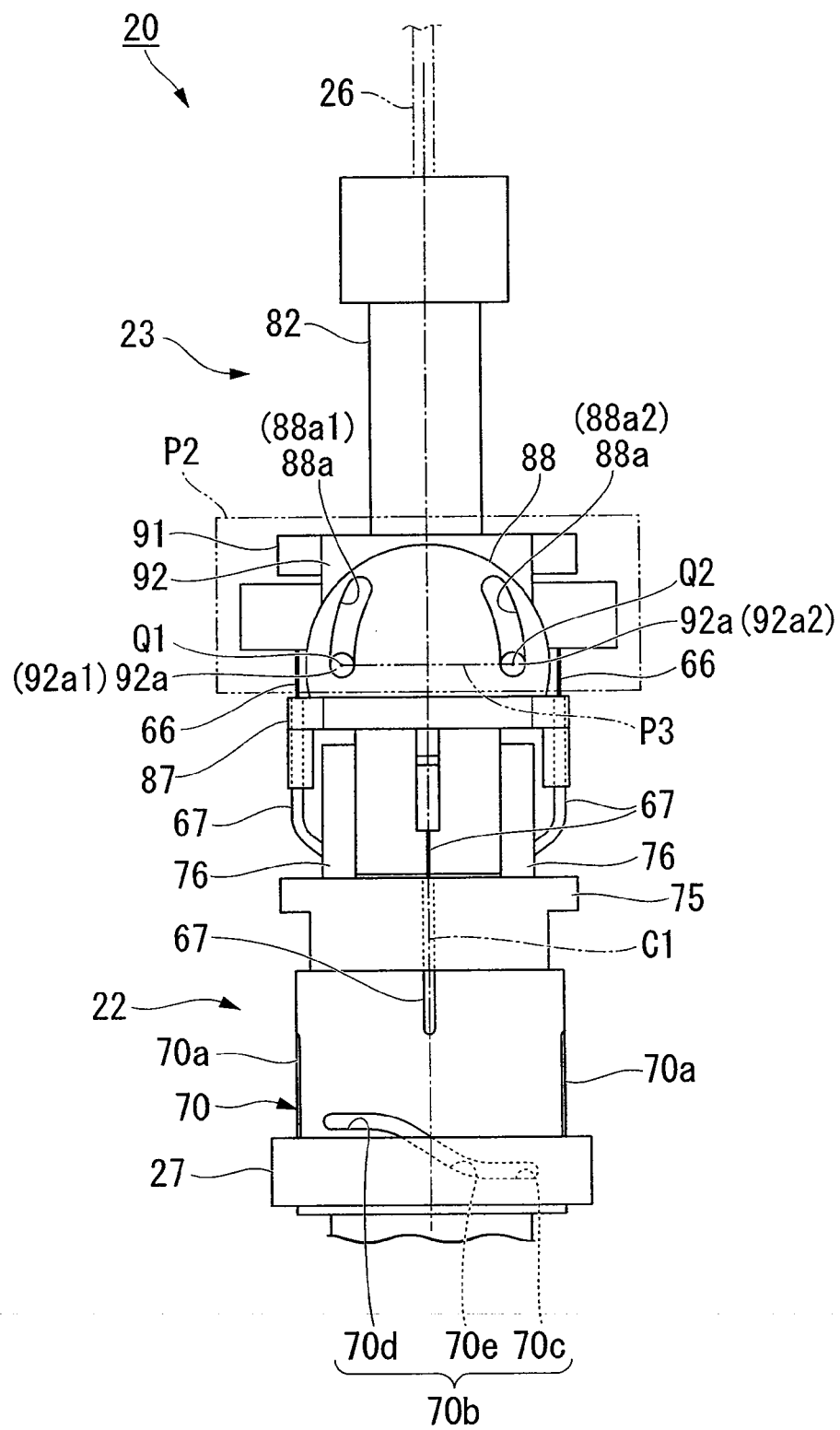
FIG. 4 is a front view showing the main part of the arm mechanism.
Figure 5:
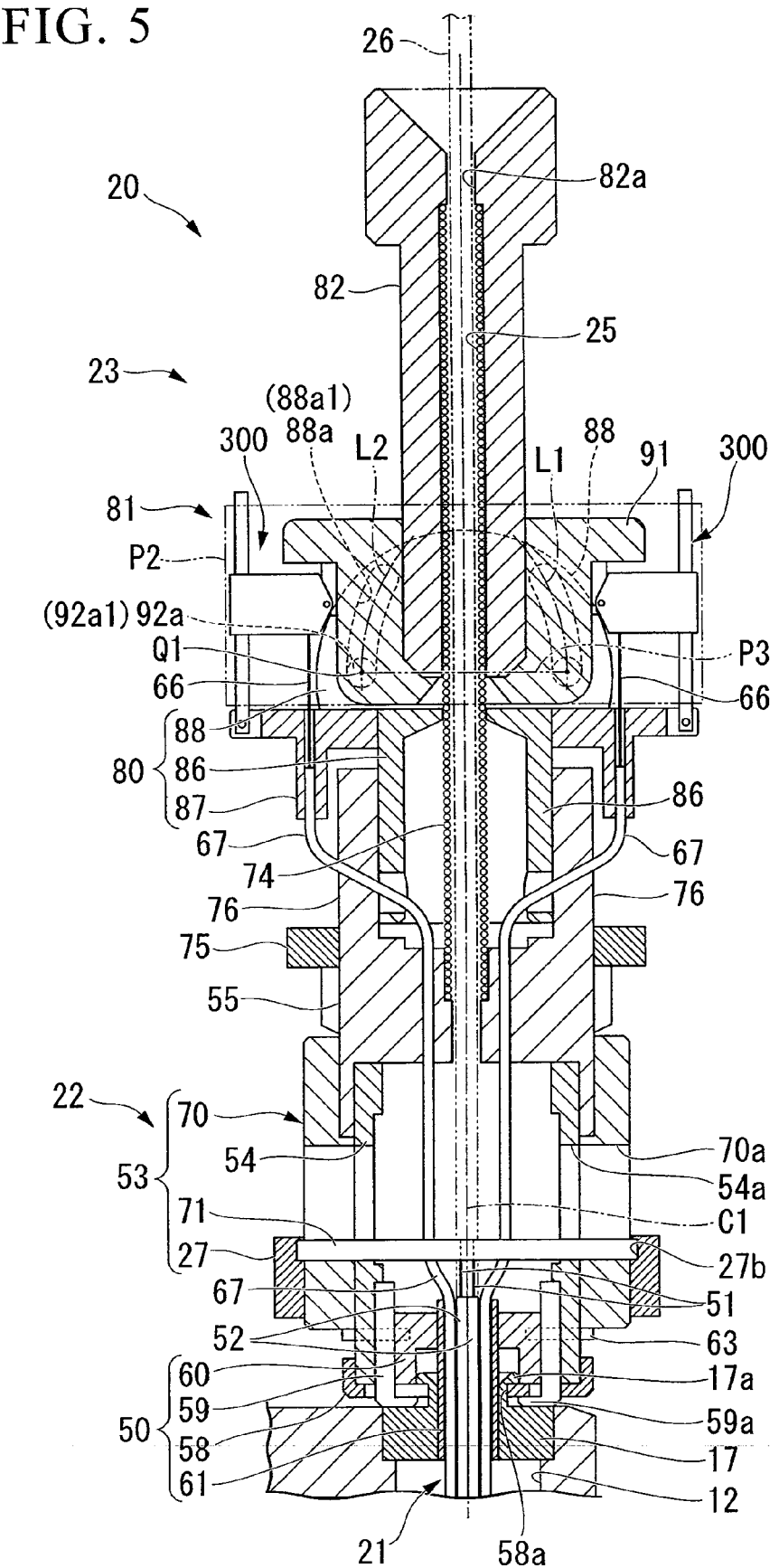
FIG. 5 is a sectional view showing the main part of the arm mechanism.

Next, the configuration of the body portion 22 and the arm manipulating portion 23 of the arm mechanism 20 will be described with reference to FIGS. 3 to 5. In addition, for convenience of description, FIGS. 3 to 5 show a state where a second curve manipulating ring 27 to be described later is pushed down. Further, since the clamps 12 and 13 have the same configuration, the clamp 12 will be described.

The body portion 22 includes an engagement mechanism 50 which engages with an opening metal 17 of the clamp opening 12, a second curve manipulating mechanism 53 which pulls a base end of a second curve manipulating wire 51, a first substantially cylindrical body member 54 which is attached with the engagement mechanism 50 and the second curve manipulating mechanism 53, and a second substantially cylindrical body member 55 which is coaxially fixed to the base end of the first body member 54 and supports the arm manipulating portion 23 in an oscillating manner.

The engagement mechanism 50 includes a slide member 58 which is formed in a plate shape and engages with the opening metal 17, a guide ring 59 which supports the slide member 58, a substantially cylindrical support member 60 which supports the slide member 58 between the guide ring 59 and the support member 60, and a tubular connection pipe 61 which is disposed on the axis C1 of the body portion 22 and is fixed to the support member 60 so as to be connected to the arm portion 21.

A substantially circular hole portion 58a is formed in the center portion of the slide member 58. When the slide member 58 moves in a direction perpendicular to the axis C1 of the body portion 22, the hole portion 58a engages with a circular flange portion 17a formed in the opening metal 17 so that the engagement mechanism 50 of the body portion 22 is fixed to the clamp opening 12. The guide ring 59 is made of, for example, metal such as stainless steel, and includes a substantially cylindrical body portion and an annular claw portion 59a which protrudes from one end of the body portion to the inside in the radial direction and interposes the slide member 58 between the flange portion 17a and the claw portion 59a.

In addition, the first body member 54, the guide ring 59, and the support member 60 are fixed from the side surface of the first body member 54 by a pin member 63. Further, the second curve manipulating sheath 52 and the arm portion manipulating sheath 67 are fixed to the connection pipe 61.

Likewise, since the guide ring 59 is made of metal such as stainless steel, even when large torque acts on the arm mechanism 20 about the hole portion 58a of the slide member 58 upon oscillating the arm manipulating portion 23, it is possible to prevent the claw portion 59a of the guide ring 59 from being damaged, where particularly large torque acts on the claw portion.

The second curve manipulating mechanism 53 includes a cylindrical guide member 70 which is fixed to the outer radial portion of the first body member 54, a second annular curve manipulating ring 27 which is disposed in the outer radial portion of the guide member 70, and a bar member 71 which is locked to the second curve manipulating ring 27 so as to be movable along the axis C1 and is attached with the base end of the second curve manipulating wire 51.

The side surfaces of the guide member 70 and the first body member 54 are respectively provided with a pair of slits 70a and 54a formed along the axis C1 and communicating with each other so as to face each other.

In the outer peripheral surface of the guide member 70, groove portions 70b are formed at two opposing positions. In more detail, in the groove portion 70b, a first groove portion 70c and a second groove portion 70d formed in a surface perpendicular to the axis C1 are connected to a third spiral groove portion 70e in a sequential order of the first groove portion 70c, the third groove portion 70e, and the second groove portion 70d so as to be formed in a substantially spiral shape as a whole, where the third spiral groove portion 70e is formed in a spiral shape so as to be close to the base end thereof when rotating in a direction depicted by E1 about the axis C1.

Particularly, as shown in FIG. 3, the inner peripheral surface of the second curve manipulating ring 27 is provided with a pair of convex portions 27a protruding inward in the radial direction so as to face each other, and the pair of convex portions 27a engages with the groove portions 70b of the guide member 70. In addition, the inner peripheral surface of the second curve manipulating ring 27 is provided with a pair of groove portions 27b formed at opposing positions so as to extend in the circumferential direction. The bar member 71 is inserted through the slit 70a of the guide member 70 and the slit 54a of the first body member 54 so as to be locked to the groove portion 27b of the second curve manipulating ring 27 at both ends of the bar member 71.

Since the second curve manipulating mechanism 53 has the above-described configuration, when the second curve manipulating ring 27 disposed at a position shown in FIGS. 3 to 5 is rotated in a direction depicted by E1 about the axis C1, the second curve manipulating ring 27 moves to the base end of the body portion 22 while rotating in a direction depicted by E1 as the convex portion 27a moves to the base end of the body portion 22 along the groove portion 70b. Since the bar member 71 is locked to the groove portion 27b of the second curve manipulating ring 27 and is inserted through the slit 70a and the slit 54a, both ends of the bar member 71 move in the inside of the groove portion 27b in the circumferential direction of the second curve manipulating ring 27, and the bar member 71 moves to the base end along the slit 70a without rotating in a direction depicted by E1. Likewise, the bar member 71 is capable of pulling the base end of the second curve manipulating wire 51 without twisting the second curve manipulating wire 51. In addition, when the convex portion 27a arrives at the second groove portion 70d of the groove portion 70b, the second curve manipulating ring 27 is fixed to the guide member 70 by means of the friction between the convex portion 27a and the second groove portion 70d. Even when the second curve manipulating ring 27 is separated from the hand of the surgeon, the second curve manipulating wire 51 is maintained in a pulled state.

As shown in FIGS. 3 to 5, the second body member 55 includes a spring member 74 which is disposed inside the second body member 55 so as to extend to the base end along the axis C1 and of which one end is fixed, a first substantially flat sheath attachment member 75 which is disposed in the outer peripheral surface of the base end of the second body member 55 and is attached with the pair of arm portion manipulating sheaths 67, and a pair of first guide members (holding members) 76 which is disposed in the surface of the base end side of the second body member 55 and is provided with a pair of slits (first and second groove portions) 76a engaging with a first oscillating portion 80 to be described later. In addition, the shape of each slit 76a will be described later in detail.

Further, the arm manipulating portion 23 includes a first oscillating portion 80 which is connected to the first guide member 76 and oscillates on a plane (first imaginary plane) P1 including the axis C1, a second oscillating portion 81 which is connected to the first oscillating portion 80 and oscillates on a plane (first imaginary plane) P2 perpendicular to the plane P1 including the axis C1, and a cylindrical manipulation stick (oscillating body) 82 which is fixed to the second oscillating portion 81. The first oscillating portion 80, the second oscillating portion 81, and the manipulation stick 82 are sequentially disposed on the axis C1 of the body portion 22.

The first oscillating portion 80 includes a first plate-shaped wire attachment plate 85 of which both ends are attached with a base end of an arm portion manipulating wire 66, a pair of first support members 86 which is fixed with the first wire attachment plate 85 therebetween and is provided with a pair of cylindrical shaft members (first and second convex portions) 86a engaging with the slits 76a of the first guide member 76, a second substantially flat-plate-shaped sheath attachment member 87 which is disposed in the outer peripheral surfaces of the base ends of the pair of first support members 86 and is attached with the pair of arm portion manipulating sheaths 67, and a pair of second plate-shaped guide members (holding bodies) 88 which is disposed in the surface of the base end side of the pair of first support members 86 and is provided with a pair of slits (first and second groove portions) 88a engaging with the second oscillating portion 81 to be described later. The first wire attachment plate 85 and the pair of first support members 86 constitute an oscillating body.

The first wire attachment plate 85, the pair of first support members 86, and the pair of first guide members 76 are formed to be symmetrical to each other with respect to the plane P1. Each of the arm portion manipulating wires 66 extends to the front end (the other side) of the arm portion 21 through one shaft member 86a and the other shaft member 86a.

The pair of shaft members 86a are formed away from each other so as to protrude from the first support member 86. In addition, when the pair of shaft members 86a engages with the slits 76a of the pair of first guide members 76 so that the slit 76a guides the shaft member 86a, the first support member 86 is regulated so as to oscillate along the plane P1.

In addition, the second oscillating portion 81 includes a second plate-shaped wire attachment plate 91 of which both ends are attached with the base ends of the arm portion manipulating wires 66 and a pair of second support members 92 which is fixed with the second wire attachment plate 91 interposed therebetween and is provided with a pair of cylindrical shaft members 92a engaging with the slits 88a of the second guide member 88. The second wire attachment plate 91, the pair of second support members 92, and the manipulation stick 82 constitute an oscillating body.

The second wire attachment plate 91, the pair of second support members 92, and the pair of second guide members 88 are formed to be symmetrical to each other with respect to the plane P2. In the front end of the second wire attachment plate 91, a pair of holding mechanisms 300 are formed so as to be symmetrical to each other with the axis C1 interposed therebetween (particularly, see FIG. 5). In addition, the detailed description thereof is omitted, and the holding mechanisms 300 are formed in the first wire attachment plate 85 in the same manner.

Figure 6:
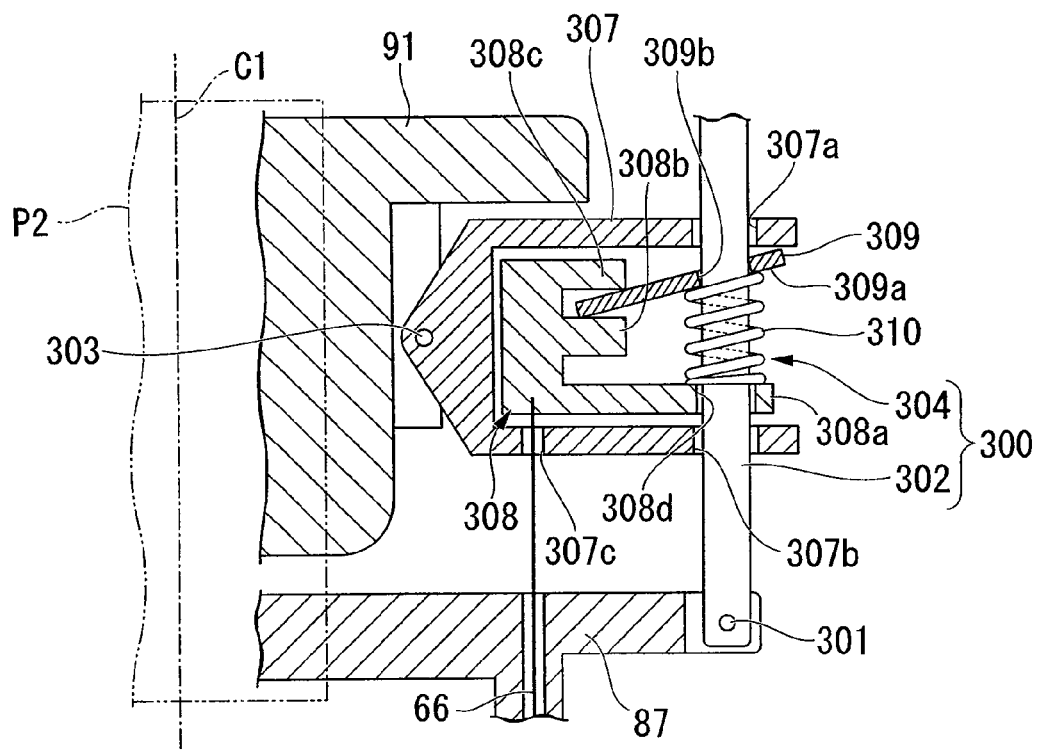
FIG. 6 is a sectional view showing the periphery of a holding mechanism of the arm mechanism.

As shown in FIG. 6, each holding mechanism 300 includes a bar-shaped shaft 302 of which one end is rotatably attached to the end of the second sheath attachment member 87 through a pin 301, and a holding portion 304 which is rotatably attached to the second wire attachment plate 91 through a pin 303 and slidably engages with the shaft 302.

In addition, the holding portion 304 includes a stopper casing 307 which has a substantially C-shaped section taken along the plane P2, a stopper base 308 which is accommodated in the stopper casing 307, a plate-shaped stopper 309 which engages with the shaft 302, and an elastic member 310 such as a spring which urges so that the stopper base 308 and one end 309a of the stopper 309 are away from each other.

The shaft 302 is disposed substantially parallel to the axis C1. The shaft 302 and the stopper casing 307 are adapted to rotate on the plane P2.

Both ends of the substantially C-shaped stopper casing 307 are provided with passage holes 307a and 307b, and the shaft 302 is inserted through the passage holes 307a and 307b. In addition, an insertion hole 307c is formed in the stopper casing 307 on the side of the axis C1 so as to extend from the lumen of the stopper casing 307 to the front end thereof.

The stopper base 308 is formed to have a substantially E-shaped section taken along the plane P2. The stopper base 308 includes a first partition plate 308a, a second partition plate 308b, and a third partition plate 308c which are disposed so as to be substantially perpendicular to the axis C1 and are sequentially disposed from the front end of the stopper base to the base end thereof, where the ends on the side of the axis C1 are integrally fixed to each other. The first partition plate 308a extends in a direction away from the axis C1 more than the second partition plate 308b and the third partition plate 308c, and the front end thereof is provided with a passage hole 308*d* for allowing the shaft 302 to be inserted therethrough. In addition, the first partition plate 308*a* of the stopper base 308 is attached with the base end of the arm portion manipulating wire 66. A gap between the second partition plate 308*b* and the third partition plate 308*c* is set to be thicker than the thickness of the stopper 309.

As described below, when the arm manipulating portion 23 is manipulated, the stopper casing 307 rotates about the pin 303 relative to the shaft 302, or the stopper base 308 moves in the inside of the stopper casing 307. However, even in this case, each of the passage holes 307*a* and 307*b* of the stopper casing 307 and the passage hole 308*d* of the stopper base 308 is set to have an inner diameter in which the passage holes are not locked to the shaft 302 so that the shaft 302 is freely inserted therethrough.

A passage hole 309*b* is formed in one end 309*a* of the stopper 309, and the shaft 302 is inserted through the passage hole 309*b*. The other end of the stopper 309 is disposed between the second partition plate 308*b* and the third partition plate 308*c* of the stopper base 308, and the above-described elastic member 310 is disposed between one end 309*a* of the stopper 309 and the first partition plate 308*a* of the stopper base 308. When one end 309*a* of the stopper 309 is urged to the base end by the elastic member 310, the other end of the stopper 309 is locked between the second partition plate 308*b* and the third partition plate 308*c* so that one end 309*a* is disposed to be inclined toward the base end with respect to the other end of the stopper 309.

Since the inner diameter of the passage hole 309*b* of the stopper 309 is set to be slightly larger than the outer diameter of the shaft 302, when the stopper 309 is disposed at a position substantially perpendicular to the shaft 302, the shaft 302 is freely inserted through the passage hole 309*b*. When the stopper 309 is inclined at a predetermined angle or more with respect to the position perpendicular to the shaft 302, the outer peripheral edge of the passage hole 309*b* is jammed in the shaft 302 so that the stopper 309 is adhered and fixed to the shaft 302. That is, in FIG. 6, the base end of the arm portion manipulating wire 66 is fixed to the second sheath attachment member 87.

Returning to FIGS. 3 to 5, the description is continued. Each of the arm portion manipulating wires 66 extends to the front end of the arm portion 21 through one shaft member 92*a* or the other shaft member 92*a*.

The pair of shaft members 92*a* are formed away from each other so as to protrude from the second support member 92. In addition, when the pair of shaft members 92*a* engages with the slits 88*a* of the pair of second guide members 88 so that the slit 88*a* guides the shaft member 92*a*, the second support member 92 is regulated to oscillate along the plane P2.

Further, the pair of arm portion manipulating wires 66 for bending the first curve 43 of the arm portion 21 in two directions on a line with respect to the axis is attached to both ends of the first wire attachment plate 85, and the pair of arm portion manipulating wires 66 for bending the first curve 43 in two directions perpendicular to the two directions is attached to both ends of the second wire attachment plate 91. In addition, a position of the first wire attachment plate 85 attached with the base ends of the pair of arm portion manipulating wires 66 moves on the plane P1, and a position of the second wire attachment plate 91 attached with the base ends of the pair of arm portion manipulating wires 66 moves on the plane P2.

Further, the other end of the spring member 74 of which one end is fixed to the second body member 55 is fixed to a perforation hole (oscillating-body-side channel) 82*a* coaxially formed with the manipulation stick 82 disposed on the axis C1 through a gap between the pair of first support members 86 and a gap between the pair of second support members 92. Likewise, the channel 25 is formed so as to include the perforation hole (insertion-portion-side channel) 21*a* (see FIG. 2) formed in the arm portion 21, the inside of the first body member 54, the inside of the second body member 55, and the inner surface of the spring member 74, and the treatment tool 26 is inserted through the channel 25 up to the arm portion 21.

As described above, a relationship between the slit 76*a* of the first guide member 76 oscillating the first oscillating portion 80 and the shaft member 86*a* of the first support member 86 and a relationship between the slit 88*a* of the second guide member 88 oscillating the second oscillating portion 81 and the shaft member 92*a* of the second support member 92 are set to have the same configuration as each other when rotating by 90° in a direction seen from the axis C1. That is, in the arm manipulating portion 23 of the arm mechanism 20 according to this embodiment, the oscillating body and the holding body make a pair, and two pairs thereof are disposed at positions shifted in the direction of the axis C1 so as to be perpendicular to the oscillating planes P1 and P2. In addition, the oscillating body including the first wire attachment plate 85 and the pair of first support members 86 and the holding body including the second guide member 88 are integrally formed with each other.

Therefore, hereinafter, a relationship between the slit 88*a* and the shaft member 92*a* will be described. In addition, only for convenience of description, the pair of slits 88*a* and the shaft members 92*a* are described as slits 88*a*1 and 88*a*2 and shaft members 92*a*1 and 92*a*2 having separate reference numerals.

When the first curve 43 of the arm portion 21 is formed in a shape along the axis of the arm portion 21, as shown in FIG. 5, the pair of shaft members 92*a*1 and 92*a*2 are disposed so as to be symmetrical to each other with respect to the axis C1 of the body portion 22 and protrudes in a direction perpendicular to the plane P2 when viewed from a plane perpendicular to the plane P2.

Here, as shown in FIGS. 3 to 5, a manipulation reference plane P3 is set so as to be perpendicular to the axis C1 and to pass through the center point (start point) Q1 of the shaft member 92*a*1 and the center point (start point) Q2 of the shaft member 92*a*2. In addition, as shown in FIG. 3, planes (second imaginary planes) P4 are set in the inner surfaces of the pair of second guide members 88.

At this time, the pair of planes P4 is parallel to the plane P2, and the pair of second guide members 88 is disposed on the plane P2.

In addition, the slit 88*a*1 is formed in an elongate hole shape so as to extend to the base end (one side) of the body portion 22 along a circular arc L2 passing through the position of the perforation hole from the center point Q1 as one end about the shaft member 92*a*2. In the same manner, the slit 82*a*2 is formed in an elongate hole shape so as to extend to the base end along a circular arc L1 passing through the position of the perforation hole from the center point Q2 as one end about the shaft member 92*a*1. In addition, when the first curve 43 of the arm portion 21 is formed in a shape taken along the axis, and the manipulation stick 82, the first oscillating portion 80, and the second oscillating portion 81 are disposed on the axis C1 of the body portion 22 (hereinafter, the position of the manipulation stick 82 is referred to as "a neutral position"), predetermined tension acts on four arm portion manipulating wires 66 so that the shaft member 92a1 and the shaft member 92a2 are respectively located at ends of the center points Q1 and Q2.

Further, as shown in FIG. 1, since the arm manipulating portion 23 is disposed in the vicinity of the switch 30 and the angle knob 31 of the endoscope manipulating portion 2, for example, one surgeon is capable of manipulating the arm manipulating portion 23, the switch 30, the angle knob 3, and the like using one hand while supporting the endoscope manipulating portion 2 using the other hand.

Next, a sequence of cutting, for example, a target tissue inside a digestive canal by using the endoscope device 1 with the above-described configuration will be described.

First, the endoscope inserting portion 3 is inserted from a patient's mouth into a body while observing a forward situation of the endoscope inserting portion 3 through the observation mechanism 6 and the monitor 15 by illuminating the forward area of the endoscope inserting portion 3 using the illumination mechanism 5. At this time, the third curve 32 of the endoscope inserting portion 3 is inserted into the body while being curved with respect to the axis C0 by an operation of rotating the angle knob 31 if necessary.

At this time, the arm mechanisms 20 may not be inserted through the lumens 8 and 9.

As shown in FIG. 2, when it is observed that the front end of the endoscope inserting portion 3 arrives at a target tissue K by using the monitor 15, the position of the front end of the endoscope inserting portion 3 is fixed, and the arm portions 21 having the treatment tools 26 inserted through the first and second lumens 8 and 9 are inserted. Then, when the slide members 58 of the engagement mechanisms 50 engage with the opening metals 17 of the clamp openings 12 and 13, the body portions 22 of the arm mechanisms 20 are attached to the clamp openings 12 and 13. Then, each of the arm portions 21 protrudes from the passageway 4a of the side surface of the endoscope inserting portion 3 by a predetermined length.

Figure 7:
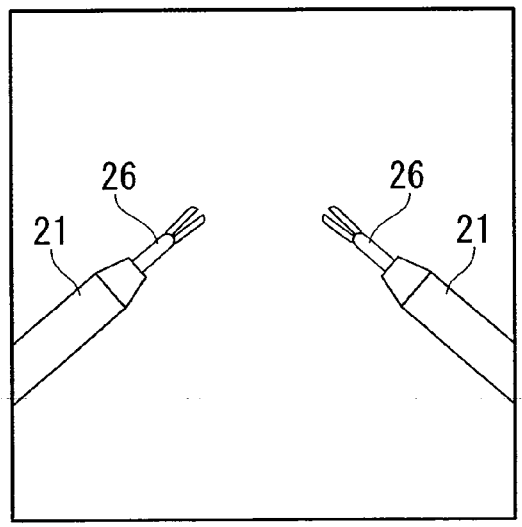
FIG. 7 is an explanatory diagram showing an observed image through a monitor of the endoscope device.

Here, the base ends of the pair of second curve manipulating wires 51 are pulled by the bar member 71 by rotating the second curve manipulating ring 27 in a direction depicted by E1, and the pair of second curves 42 are fixed while being bent in an S shape so as to face each other. At this time, as shown in FIG. 7 showing the image of the monitor 15, a so-called triangular arrangement is formed such that the front ends of the treatment tools 26 are close to each other and the base ends of the arm portions 21 are opened, thereby easily performing a surgical technique.

In addition, in this embodiment, since the substantially circular hole portion 58a of the slide member 58 of the body portion 22 engages with the circular flange portion 17a of the opening metal 17, it is possible to adjust the curving direction of the arm portion 21 by rotating the arm manipulating portion 23 and the body portion 22 of the arm mechanism 20 about the axis C1 of the body portion 22 relative to each of the lumens 8 and 9. Independently from this rotation, it is possible to rotate the treatment tool 26 about the axis relative to the arm mechanism 20. If necessary, the surgeon manipulates the manipulation stick 82 so as to adjust a curving direction of the arm portion 21 and a direction of the treatment tool 26 as described later in detail.

Next, the surgeon performs a treatment on the target tissue K. First, the treatment tool 26 is reciprocated relative to the manipulation stick 82 of one arm mechanism 20 or the manipulation stick 82 is oscillated relative to the body portion 22 in order to grip the endoscope manipulating portion 2 using one hand and to adjust the position or direction of the front end of the arm portion 21 using the other hand. When the treatment tool 26 is reciprocated relative to the manipulation stick 82, it is possible to adjust a protruding length of the treatment tool 26 from the front end of the arm portion 21. Then, when the manipulation stick 82 is oscillated relative to the body portion 22, as described below, it is possible to bend the first curve 43 in four directions with respect to the axis of the arm portion 21.

Figure 8:
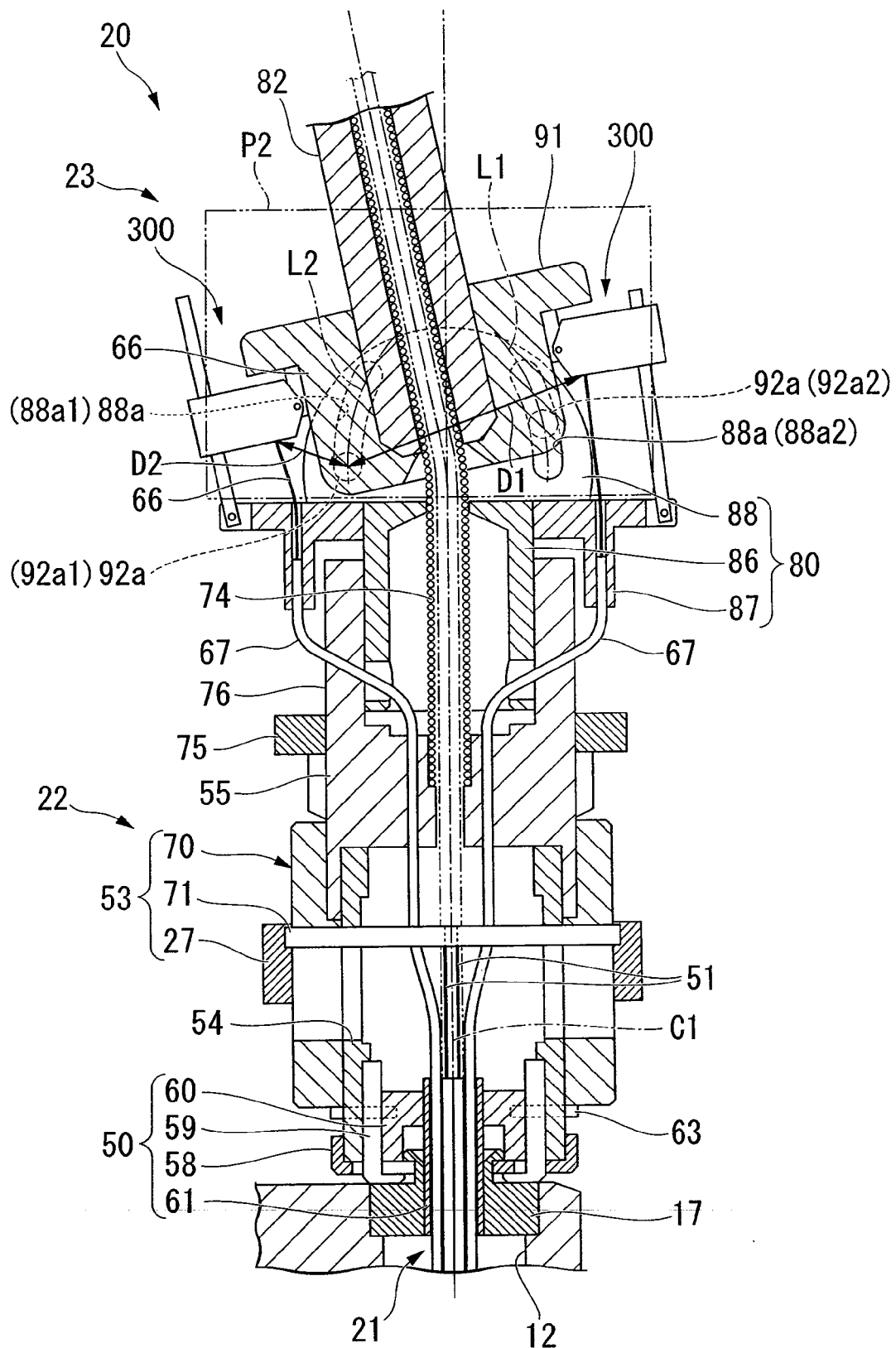
FIG. 8 is a sectional view showing an operation of the main part of the arm mechanism.

That is, as shown in FIG. 8, for example, when the manipulation stick 82 of the arm mechanism 20 moves down toward the slit 88a1, the second wire attachment plate 91 rotates about the shaft member 92a1.

Figure 9:
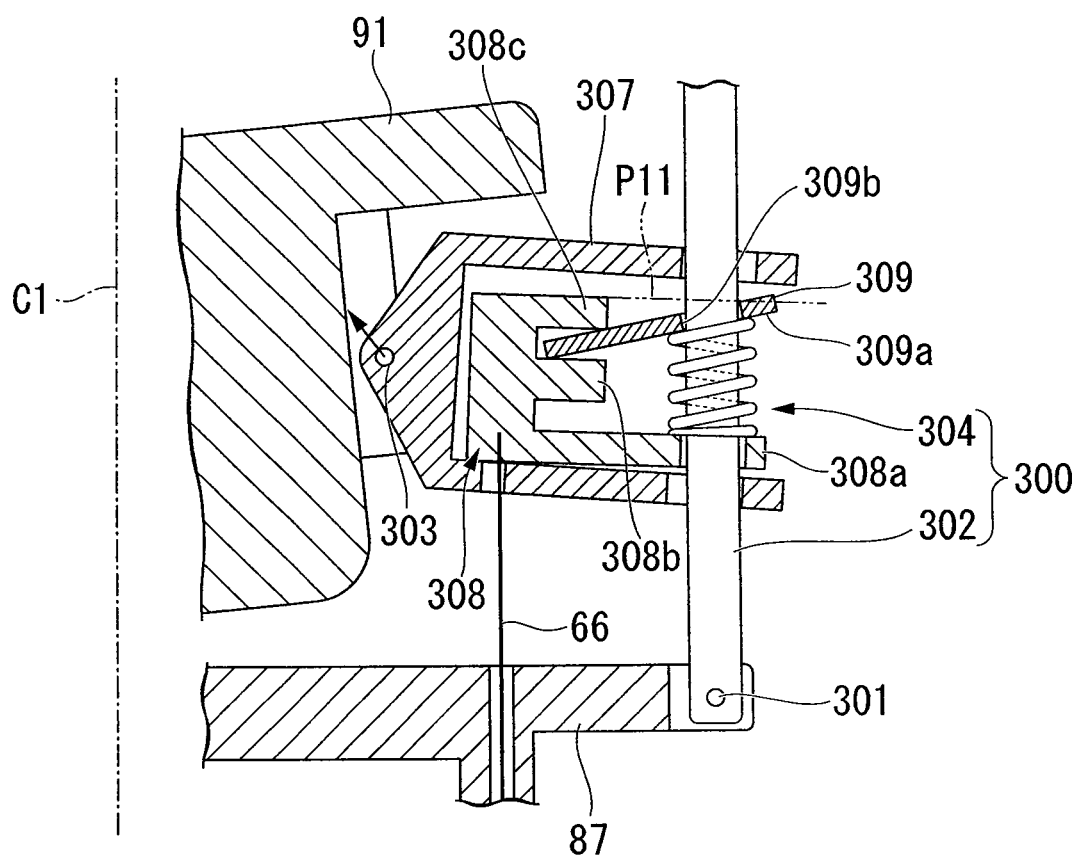
FIG. 9 is a sectional view showing an operation in the periphery of the holding mechanism of the arm mechanism.

At this time, in the holding mechanism 300 disposed in the slit 88a1, as shown in FIG. 9, the second wire attachment plate 91 and the pin 303 rotate in a direction depicted by the arrow in the drawing. Then, the front-end-side inner surface of the stopper casing 307 comes into contact with the first partition plate 308a of the stopper base 308 so as to move the stopper base 308 toward the base end. For this reason, in the state where the position of one end 309a of the stopper 309 is substantially maintained, the second partition plate 308b moves the other end of the stopper 309 toward the base end so that the stopper 309 is substantially perpendicular to the shaft 302, and hence the operation of fixing the stopper 309 to the shaft 302 is canceled.

When the surgeon's hand is release from the manipulation stick 82, the second wire attachment plate 91 is slightly inclined toward the slit 88a2 due to a difference in the tension (which indicates that the tension of the pulled arm portion manipulating wire 66 becomes strong) of two arm portion manipulating wires 66 attached to the second wire attachment plate 91. Accordingly, in the state where the position of one end 309a of the stopper 309 is substantially maintained, the other end of the stopper 309 moves toward the front end so that the outer peripheral edge of the passage hole 309b is jammed in the shaft 302, and the stopper 309 is fixed to the shaft 302.

Then, as shown in FIG. 8, the arm portion manipulating wire 66 attached to the end of the second wire attachment plate 91 on the side opposite the side where the manipulation stick 82 moves down is pulled in the state where a radius is a distance D1 from the center of the shaft member 92a1 to the attachment position of the arm portion manipulating wire 66. For this reason, compared with the case where the second wire attachment plate 91 rotates about the center point between the shaft member 92a1 and the shaft member 92a2, it is possible to pull the arm portion manipulating wire 66 in a longer distance. On the other hand, the arm portion manipulating wire 66 attached to the end of the second wire attachment plate 91 on the side where the manipulation stick 82 moves down is pushed in while having a radius set to a distance D2 from the center of the shaft member 92a1 to the attachment position of the arm portion manipulating wire 66. For this reason, compared with the case where the second wire attachment plate 91 rotates about the above-described center point, it is possible to suppress the loosening amount of the arm portion manipulating wire 66.

Figure 10:
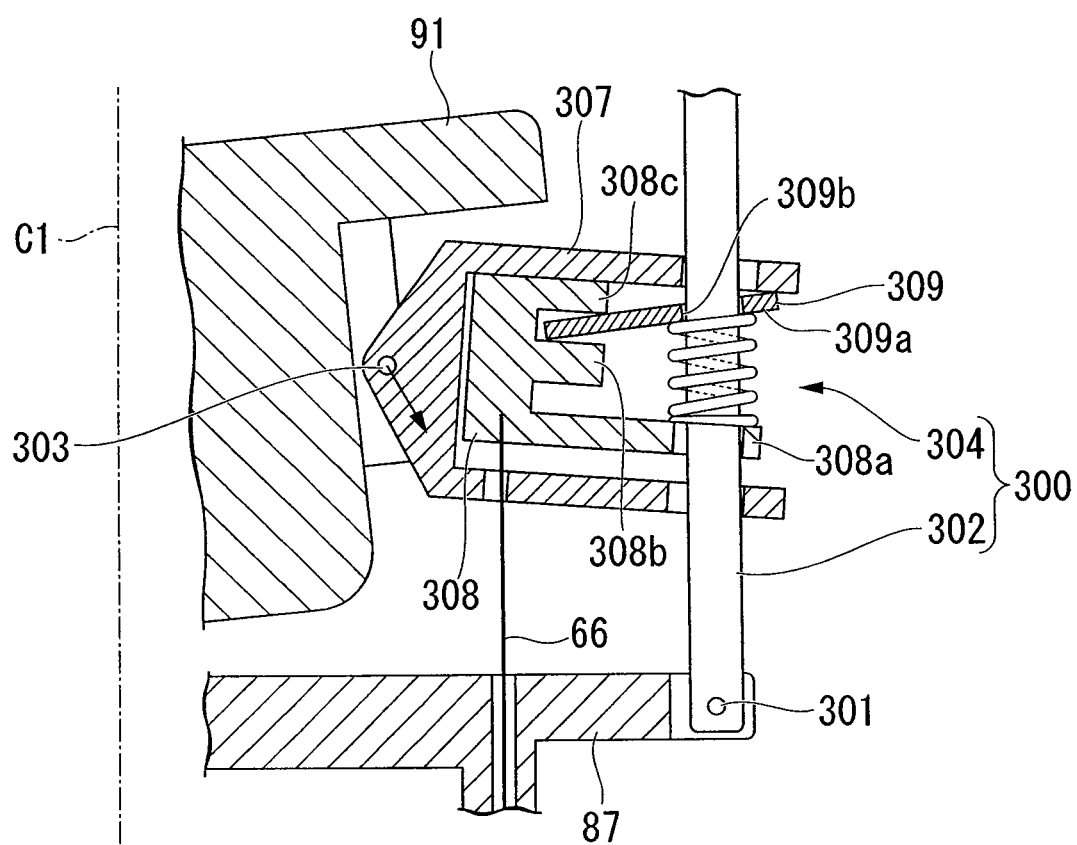
FIG. 10 is a sectional view showing an operation in the periphery of the holding mechanism of the arm mechanism.

In addition, when the manipulation stick 82 moves down toward the slit 88a2 in this state, as shown in FIG. 10, the second wire attachment plate 91 rotates in a direction depicted by the arrow in the drawing together with the pin 303. Then, the inner surface of the base end side of the stopper casing 307 comes into contact with one end 309a of the stopper 309 so as to move the base-end-side portion of the stopper 309 to the front end from a plane P11 extending from the inner surface of the base end side surface of the third partition plate 308c as shown in FIG. 9. For this reason, as shown in FIG. 10, in the state where the position of the other end of the stopper 309 is substantially maintained, the stopper casing 307 moves one end 309a of the stopper 309 toward the front end so that the stopper 309 is substantially perpendicular to the shaft 302, and hence the operation of fixing the shaft 302 to the stopper 309 is canceled.

In this manner, the second wire attachment plate 91 rotates about the shaft member 92a1.

In this embodiment, since the treatment tool 26 is reciprocated relative to the manipulation stick 82, the oscillating center of the manipulation stick 82 is located at a fixed position in the direction of the axis C1 of the body portion 22 regardless of the reciprocating movement of the treatment tool 26. That is, as shown in FIG. 1, even when the treatment tool 26 is reciprocated so that the manipulation end is located at the position Z1 or the position Z2, the position of the oscillating center Z3 of the treatment tool 26 does not change, which has such a merit that a natural oscillating movement can be performed. However, when the treatment tool 26 is oscillated in the state where the treatment tool 26 is withdrawn to the base end as much as possible, that is, in the state where the manipulation end of the treatment tool 26 is withdrawn as much as possible, the movement range of the manipulation end of the treatment tool 26 becomes wide, which may cause such a problem that the treatment tool 26 contacts with the surgeon or the endoscope manipulating portion 2.

Further, in this embodiment, since the first curve 43 of the arm portion 21 is formed in a shape of the first curve 43 taken along the axis of the arm portion 21 when the manipulation stick 82 is located at the neutral position, it is possible to easily determine the position of the manipulation stick 82 corresponding to the state where the first curve 43 is formed in a linear shape. In addition, when the first curve 43 of each arm portion 21 is formed in a shape taken along the axis of the arm portion, and the first oscillating portion 80 and the second oscillating portion 81 are disposed at positions taken along the axis C1 of the body portion 22, uniform tension acts on each of four arm portion manipulating wires 66. For this reason, the first curve 43 of the arm portion 21 is easily disposed at the stable position taken along the axis, and the manipulation stick 82 is easily disposed at the stable neutral position.

Then, the surgeon manipulates the base end of the treatment tool 26 so that the front end of the treatment tool 26 grips and pulls the target tissue K, and maintains one of arm mechanisms 20 in this state.

In addition, the surgeon manipulates the other arm mechanism 20 in the same manner so that the treatment tool 26 cuts the target tissue K.

In this embodiment, as shown in FIG. 2, when the arm portions 21 protrude forward from the endoscope inserting portion 3 so as to bend the second curve 42 and the first curve 43, it is possible to shorten a length A3 from the front end of the treatment tool 26 to the front end surface 3a of the endoscope inserting portion 3, and thus to perform the treatment in the inside of a comparatively narrow space such as a digestive canal.

In this manner, in the arm manipulating portion 23 according to this embodiment, the pair of shaft members 92a move in the inside of the pair of slits 88a formed on the plane P4 of the second guide member 88. For this reason, it is possible to stably oscillate the manipulation stick 82, moving on the plane P2 parallel to the plane P4, along the slit 88a.

In the arm manipulating portion 23, the shaft member 92a1 rotates in the rotation direction from the center point Q1 of the slit 88a1 on the plane P2, and the shaft member 92a2 moves inside the slit 88a2 so that the manipulation stick 82 oscillates in the rotation direction from the center point Q1. However, this movement can be changed shch that the shaft member 92a2 rotates in the rotation direction from the center point Q2 of the slit 88a2, and the shaft member 92a1 moves inside the slit 88a1 so that the manipulation stick 82 oscillates in the rotation direction from the center point Q2. Accordingly, it is possible to further stabilize the oscillation of the manipulation stick 82.

In addition, since the oscillating center of the manipulation stick 82 is suppressed from changing from one of the shaft member 92a1 and the shaft member 92a2 to the other thereof when the manipulation stick 82 is inclined toward one of them at the neutral position, it is possible to further improve the operability of the manipulation stick 82.

Since the manipulation stick 82 is disposed between the pair of second guide members 88, it is possible to further reliably oscillate the manipulation stick 82 on the plane P2.

Since the oscillating body and the holding body make a pair in the arm manipulating portion 23, and two pairs thereof are disposed so that the oscillating planes of two pairs are perpendicular to each other, it is possible to oscillate the manipulation stick 82 in two directions which are perpendicular to each other.

In addition, in the arm mechanism 20 according to this embodiment, when the manipulation stick 82 is oscillated in the rotation direction from the position Q1 or the position Q2 on the plane P2, it is possible to change the pulled arm portion manipulating wires 66, and to change the curving direction of the first curve 43.

Further, since the uniform tension acts on the arm portion manipulating wires 66 at the neural position, when the external force is applied to the manipulation stick 82, the manipulation stick 82 is located on the axis C1 of the body portion 22. At this time, the shaft member 92a1 is located at the center point Q1 of the slit 88a1, and the shaft member 92a2 is located at the center point Q2 of the slit 88a2. Accordingly, it is possible to easily change the oscillating center of the manipulation stick 82.

Since the perforation hole 82a of the manipulation stick 8 communicates with the perforation hole 21a of the arm portion 21 so as to form the channel 25, it is possible to perform the treatment by inserting the treatment tool 26 into the channel 25 of the arm mechanism 20.

Since the arm portions 21, through which the treatment tools 26 are inserted, protrude from the front ends of the lumens 8 and 9 by respectively inserting the arm mechanisms 20 through the first and second lumens 8 and 9 formed in the endoscope device 1, it is possible to perform various treatments using the treatment tools 26 while bending the first curves 43 of the arm mechanisms 20.

In addition, since the arm mechanism 20 is attached to the endoscope device 1 in the state where the arm portion 21 is inserted through the first lumen 8 or the second lumen 9, it is possible to integrating the endoscope device 1 with the arm mechanism 20, and thus to improve the operability of the endoscope device.

Since the arm portions 21 of the arm mechanisms 20 are rotated in the rotation direction about the axis thereof at the front ends of the first lumen 8 and the second lumen 9, it is possible to improve the treatment operability using the endoscope device 1.

Since the first wire attachment plate 85 and the second wire attachment plate 91 are provided with the holding mechanisms 300, it is possible to easily bend the first curve 43 of the arm mechanism 20, and to maintain the curve state of the first curve 43 bent by the surgeon. Then, one surgeon is capable of easily manipulating the endoscope device 1.

In addition, as described above, since the endoscope device 1 according to this embodiment uses two arm mechanisms 20, it is possible to perform a complex treatment.

Figure 11:
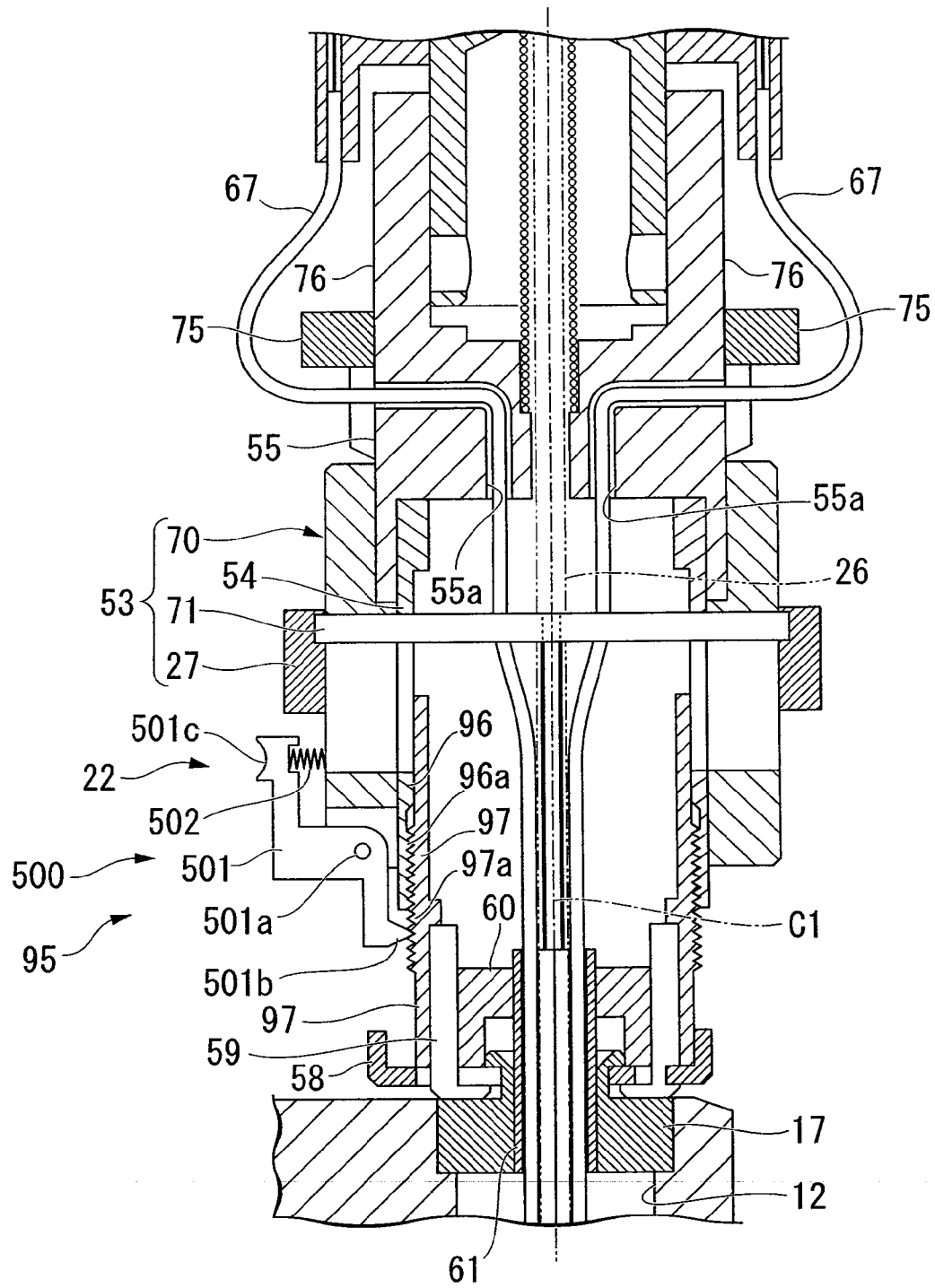
FIG. 11 is a sectional view showing a main part of the arm mechanism according to a modified example of the first embodiment of the present invention.

Further, as in the modified example shown in FIG. 11, the first body member 54 according to this embodiment may be formed by double tubes, that is, a body's base end side member 96 and a body-front-end-side member 97 which are formed in a cylindrical shape so as to have different diameters, and the inner peripheral surface of the body-base-end-side member 96 and the outer peripheral surface of the body-front-end-side member 97 coming into contact with each other may be provided with positioning portions 96a and 97a used for determining the relative position in the direction of the axis C1. In this modified example, the positioning portions 96a and 97a are formed in an concavity and a convexity so as to be continuous in the direction of the axis C1 and to be fitted to each other.

The arm portion manipulating sheathes 67 are inserted through the perforation holes 55a formed in the second body member 55.

In addition, the body-base-end-side member 96 is attached with a fixing mechanism 500 for fixing the body-base-end-side member 96 to the body-front-end-side member 97 in the direction of the axis C1. The fixing mechanism 500 includes a lever 501 which is rotatably attached to the body-base-end-side member 96 through a pin 501a and an urging member 502 which urges the lever 501 in the rotation direction of the pin 501a. The lever 501 is provided with a claw portion 501b, and the claw portion 501b is adapted to be fitted to the positioning portion 96a of the body-base-end-side member 96. In addition, the lever 501 is urged by the urging member 502 so that the claw portion 501b is fitted to the positioning portion 96a.

The body-base-end-side member 96, the body-front-end-side member 97, and the fixing mechanism 500 constitute a length adjusting mechanism 95.

Figure 12:
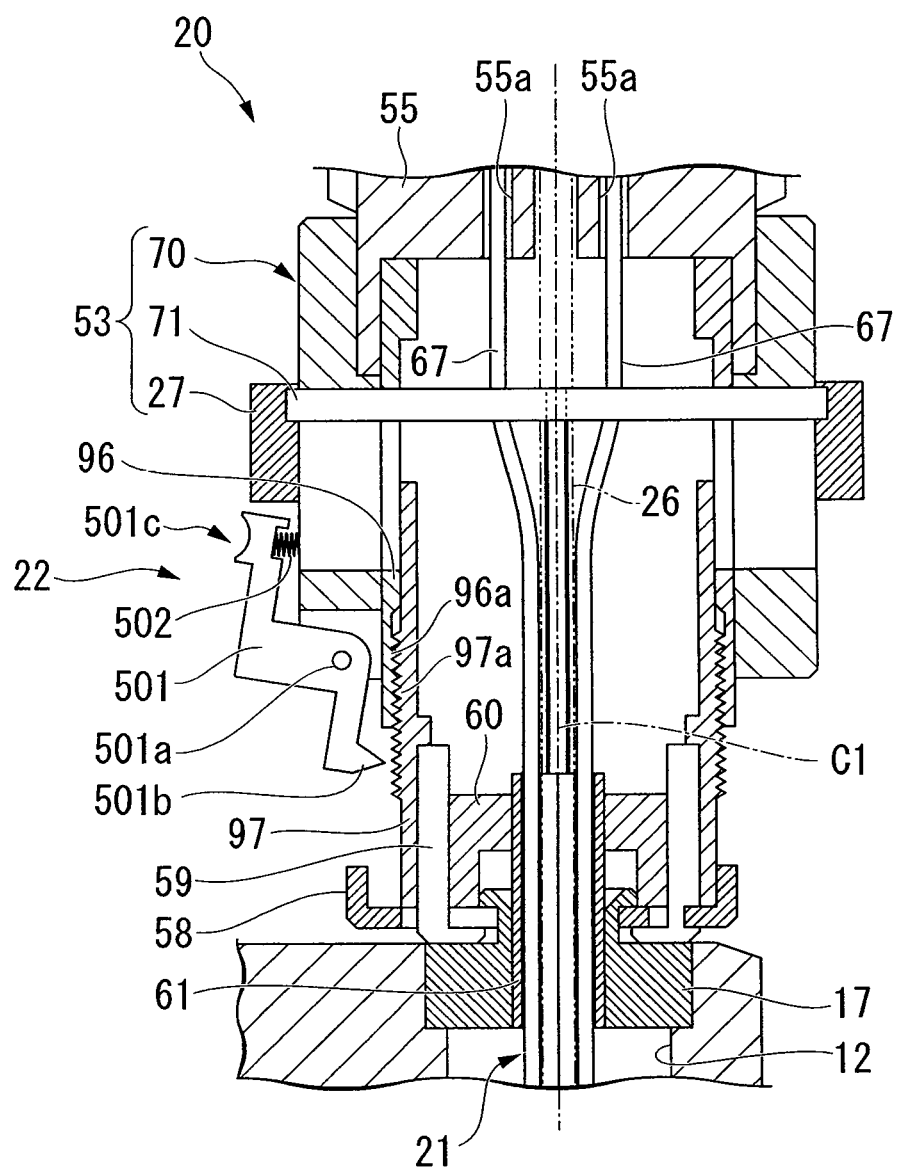
FIG. 12 is a sectional view showing an operation of the arm mechanism according to the modified example.

FIG. 11 shows a state where the body-base-end-side member 96 is fixed to the body-front-end-side member 97 in the direction of the axis C1. When a lever pressing portion 501c formed in the lever 501 is pushed toward the axis C1 against the force of the urging member 502, as shown in FIG. 12, it is possible to move the claw portion 501b and the positioning portion 96a to be away from each other. In this state, when the body-base-end-side member 96 is reciprocated in the direction of the axis C1, it is possible to change the protruding length of the treatment tool 26.

In addition, since the arm portion manipulating sheath 67 is inserted through the perforation hole 55a formed in the second body member 55 while ensuring a sufficient length, even when the body-base-end-side member 96 is reciprocated relative to the body-front-end-side member 97, it is possible to prevent the arm portion manipulating sheath 67 from continuously extending.

In this modified example, since the length of the body portion 22 of the arm mechanism 20 in the direction of the axis C1 can be adjusted, it is possible to adjust the protruding length of the treatment tool 26 from the front end of the arm portion 21 by using the positional relationship between the body-base-end-side member 96 and the body-front-end-side member 97 without changing the protruding length of the treatment tool 26 closer to the base end than the manipulation stick 82 as in the first embodiment.

Figure 13:
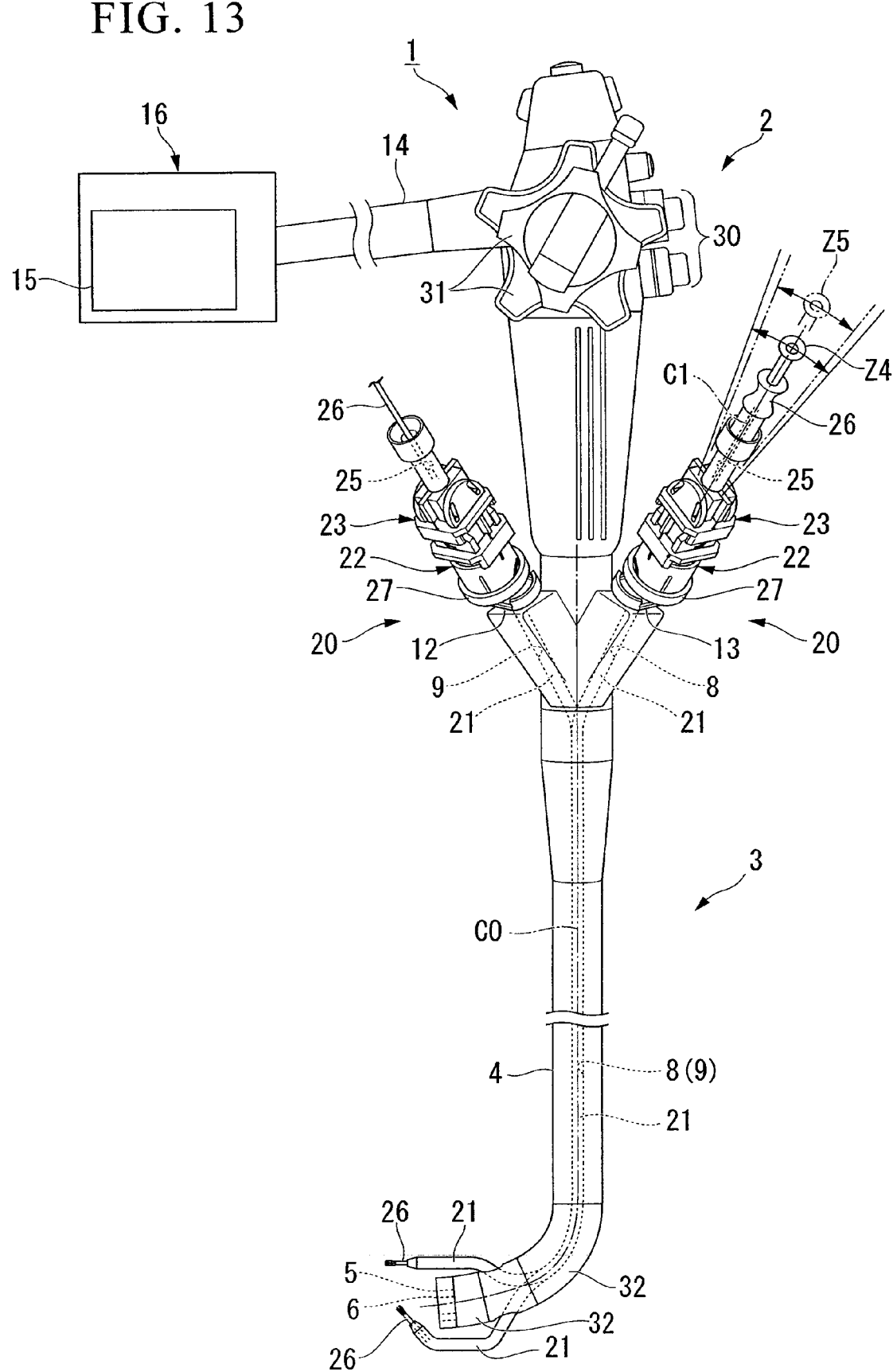
FIG. 13 is an overall view showing the endoscope device according to the modified example.

In addition, since the oscillating center of the manipulation stick 82 is reciprocated in the direction of the axis C1, as shown in FIG. 13, it is possible to allow the movement width of the manipulation end of the treatment tool 26 in a direction perpendicular to the direction of the axis C1 to be uniform regardless of the reciprocation state of the treatment tool 26 even when the manipulation end is located at the position Z4 or Z5.

However, since the position of the oscillating center deviates due to the reciprocation of the treatment tool 26, the surgeon may feel uncomfortable by manipulating the device.

Note that, in this modified example, even when the body-base-end-side member 96 rotates in the rotation direction about the axis C1 relative to the body-front-end-side member 97, this rotation is absorbed between the engagement mechanism 50 and the clamp opening 12, and hence the arm mechanism 20 does not rotate.

Also, even when the arm mechanism 20 moves in the direction of the axis C1, since the lengths of the manipulating wire 66 and the arm portion manipulating sheath 67 are fully-extended, lack of both lengths does not occur. At this time, when the arm portion 21 is fixed to the front end of the endoscope inserting portion, the arm portion 21 does not protrude from the front end of the endoscope inserting portion due to the loosening state of the manipulating wire 66 and the arm portion manipulating sheath 67.

Note that, in this embodiment, each of the pair of slits 70a and the pair of the slits 88a is formed in a circular arc shape of which a center is the center point Q1. However, the shape of the slit 88a is not limited thereto, but may be formed in a shape closer to each other in a direction away from the plane P3 to the base end of the body portion 22. The same applies to the slit 70a.

Further, in this embodiment, the arm manipulating portion 23 is provided with two pairs of the oscillating body and the holding body, where the oscillating body and the holding body make a pair. However, a pair of the oscillating body and the holding body may be disposed in the arm manipulating portion 23.

Second Embodiment

Next, a second embodiment of the invention will be described. Since the same reference numerals will be given to the same constituents as those of the above-described embodiment, the description thereof will be omitted, and only the differences will be described.

Figure 14:
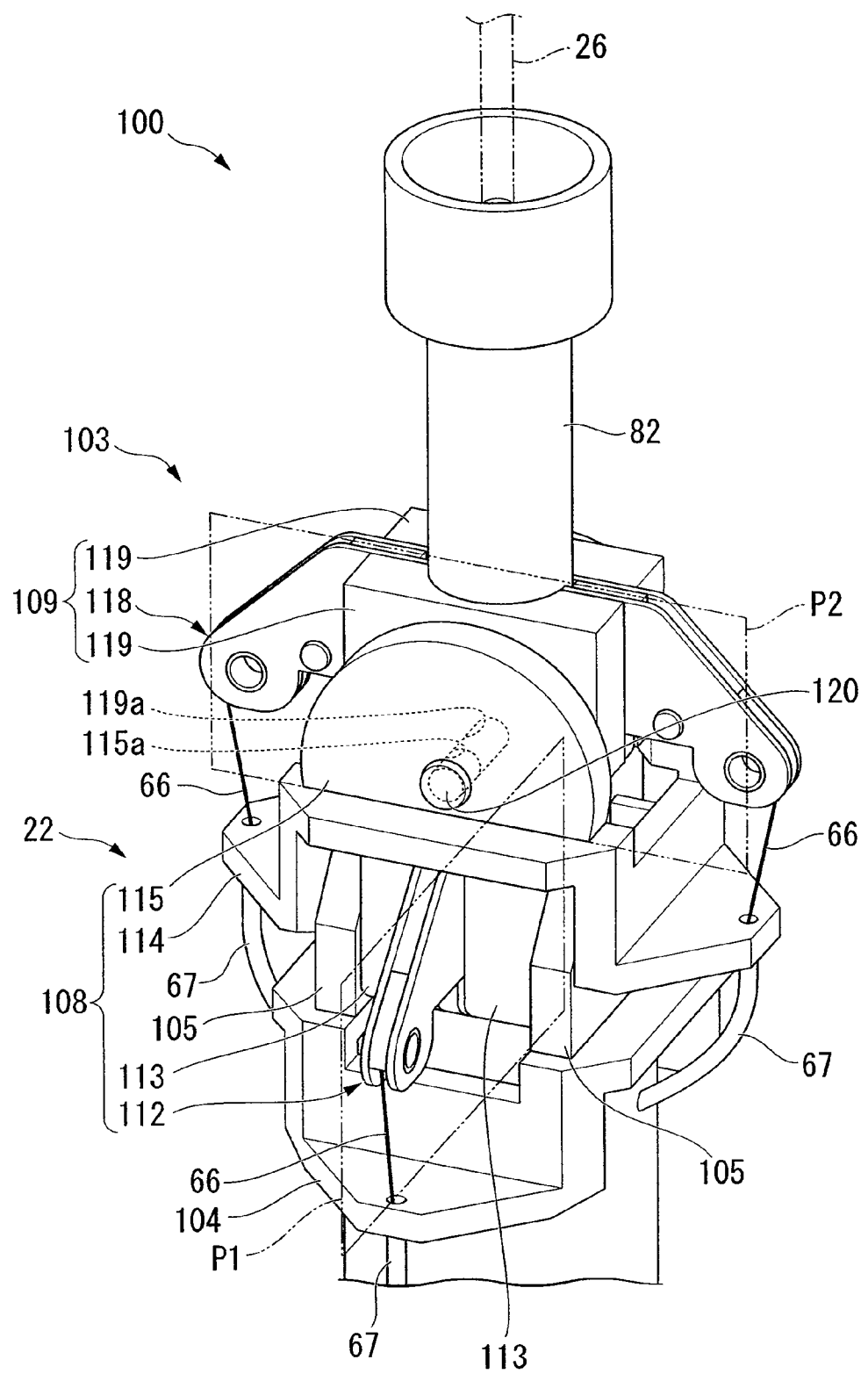
FIG. 14 is a perspective view showing a main part of the arm mechanism of the endoscope device according to a second embodiment of the present invention.
Figure 15:
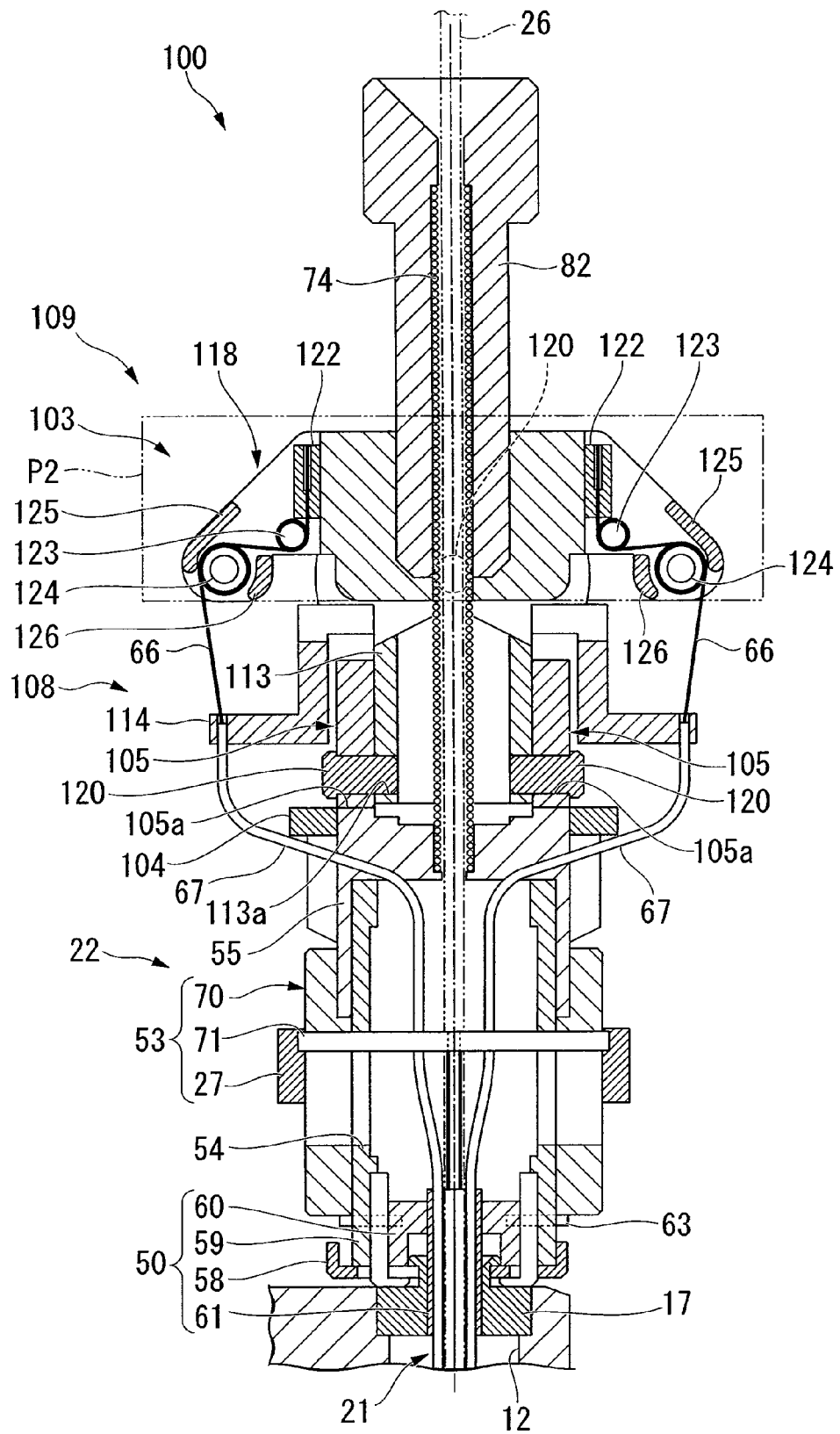
FIG. 15 is a sectional view showing the main part of the arm mechanism.

As shown in FIGS. 14 and 15, an arm mechanism 100 according to this embodiment includes the arm portion 21, the body portion 22, and an arm manipulating portion 103 which is manipulated to curve the front end of the arm portion 21.

The second body portion 55 of the body portion 22 includes the spring member 74, a first sheath attachment member 104 which is disposed in the outer peripheral surface of the base end of the second body member 55, and a pair of first plate-shaped guide members 105 which is disposed in the surface of the base end side of the second body member 55 and is provided with a perforation hole 105a so as to rotatably support a first oscillating portion 108 to be described later.

The pair of arm portion manipulating sheaths 67, through which the arm portion manipulating wires 66 are inserted, is attached to both ends of the first sheath attachment member 104.

In addition, the arm portion manipulating portion 103 includes the first oscillating portion 108 which is rotatably supported to the pair of first guide members 105 so as to oscillate on the plane P1 including the axis C1, the second oscillating portion 109 which is connected to the first oscillating portion 108 so as to oscillate on the plane P2 perpendicular to the plane P1 including the axis C1, and the cylindrical manipulation stick 82 which is fixed to the second oscillating portion 109.

The first oscillating portion 108 includes a first plate-shaped wire attachment portion 112 of which both ends are attached with the base ends of the arm portion manipulating wires 66, a pair of first support members 113 which is fixed with the first wire attachment portion 112 interposed therebetween, a second sheath attachment member 114 which is disposed in the outer peripheral surfaces of the base ends of the pair of first support members 113 and is attached with the pair of arm portion manipulating sheaths 67, and a pair of second plate-shaped guide members 115 which is disposed in the surfaces of the base end side of the pair of first support members 113 and is provided with perforation holes 115a so as to rotatably support the second oscillating portion 109.

Each of the first support members 113 is provided with a perforation hole 113a which communicates with the perforation hole 105a of the first guide member 105. In addition, both ends of the second sheath attachment member 114 are attached with the pair of arm portion manipulating sheaths 67 through which the arm portion manipulating sheaths 66 are inserted.

In addition, a pair of pin members 120 is inserted through the perforation holes 105a of the first guide members 105 and the perforation holes 113a of the first support members 113 so that the first oscillating portion 108 rotates on the plane P1 about the pin member 120 relative to the first guide member 105.

The second oscillating portion 109 includes a second plate-shaped wire attachment portion 118 of which both ends are attached with the base ends of the arm portion manipulating wires 66, and a pair of second support members 119 which is fixed with the second wire attachment portion 118 interposed therebetween and is provided with perforation holes 119a communicating with the perforation holes 115a of the second guide members 115.

In addition, the pair of pin members 120 is inserted through the perforation holes 115a of the second guide members 115 and the perforation holes 119a of the first support members 119 so that the second oscillating portion 109 rotates on the plane P2 about the pin member 120 relative to the second guide members 115.

Here, since the first wire attachment portion 112 and the second wire attachment portion 118 have the same configuration, the configuration of the second wire attachment portion 118 will be described with reference to FIG. 15.

The second wire attachment portion 118 includes a fixing member 122 which fixes the base ends of the arm portion manipulating wires 66, first and second winding members 123 and 124 around which the arm portion manipulating wires 66 are wound, and regulation members 125 and 126 which prevent the arm portion manipulating wires 66 from protruding to the outside. In addition, the arm portion manipulating wire 66 wound around the second winding member 124 extends to the inside of the arm portion manipulating sheath 67 attached to the second sheath attachment member 114.

Figure 16:
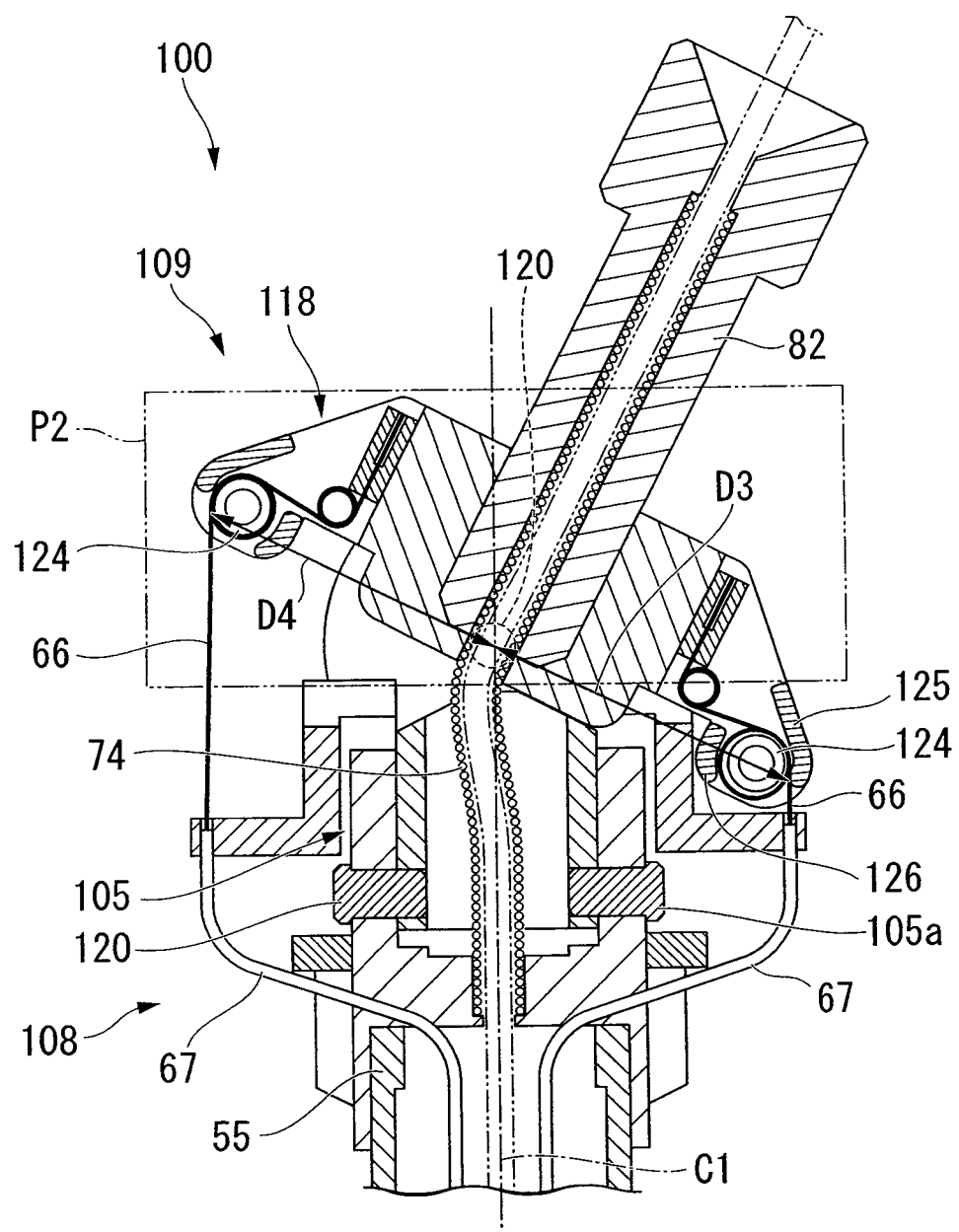
FIG. 16 is a sectional view showing an operation of the main part of the arm mechanism.

In the arm mechanism 100 having the above-described configuration, for example, as shown in FIG. 16, when the manipulation stick 82 of the arm mechanism 100 falls down along the second wire attachment portion 118, the second wire attachment portion 118 rotates on the plane P2 about the pin member 120. In addition, the arm portion manipulating wire 66 attached to the end of the second wire attachment portion 118 opposite to where the manipulation stick 82 moves down is drawn out in the state where a radius is a distance D4 from the center of the pin member 120 to the position of the second winding member 124 where the arm portion manipulating wire 66 is drawn out. On the other hand, the arm portion manipulating wire 66 attached to the end of the second wire attachment portion 118 on the side where the manipulation stick 82 falls down is pushed in while having a radius set to a distance D3 from the center of the pin member 120 to the position of the second winding member 124 where the arm portion manipulating wire 66 is drawn out. At this time, in this embodiment, since the periphery of the second winding member 124 is provided with a space for accommodating the remaining arm portion manipulating wire 66, it is possible to manipulate the arm portion manipulating wire 66 while suppressing the arm portion manipulating wire 66 from being loosened in other portions.

Third Embodiment

Next, a third embodiment of the invention will be described. Since the same reference numerals will be given to the same constituents as those of the above-described embodiment, the description thereof will be omitted, and only the different points will be described.

Figure 17:
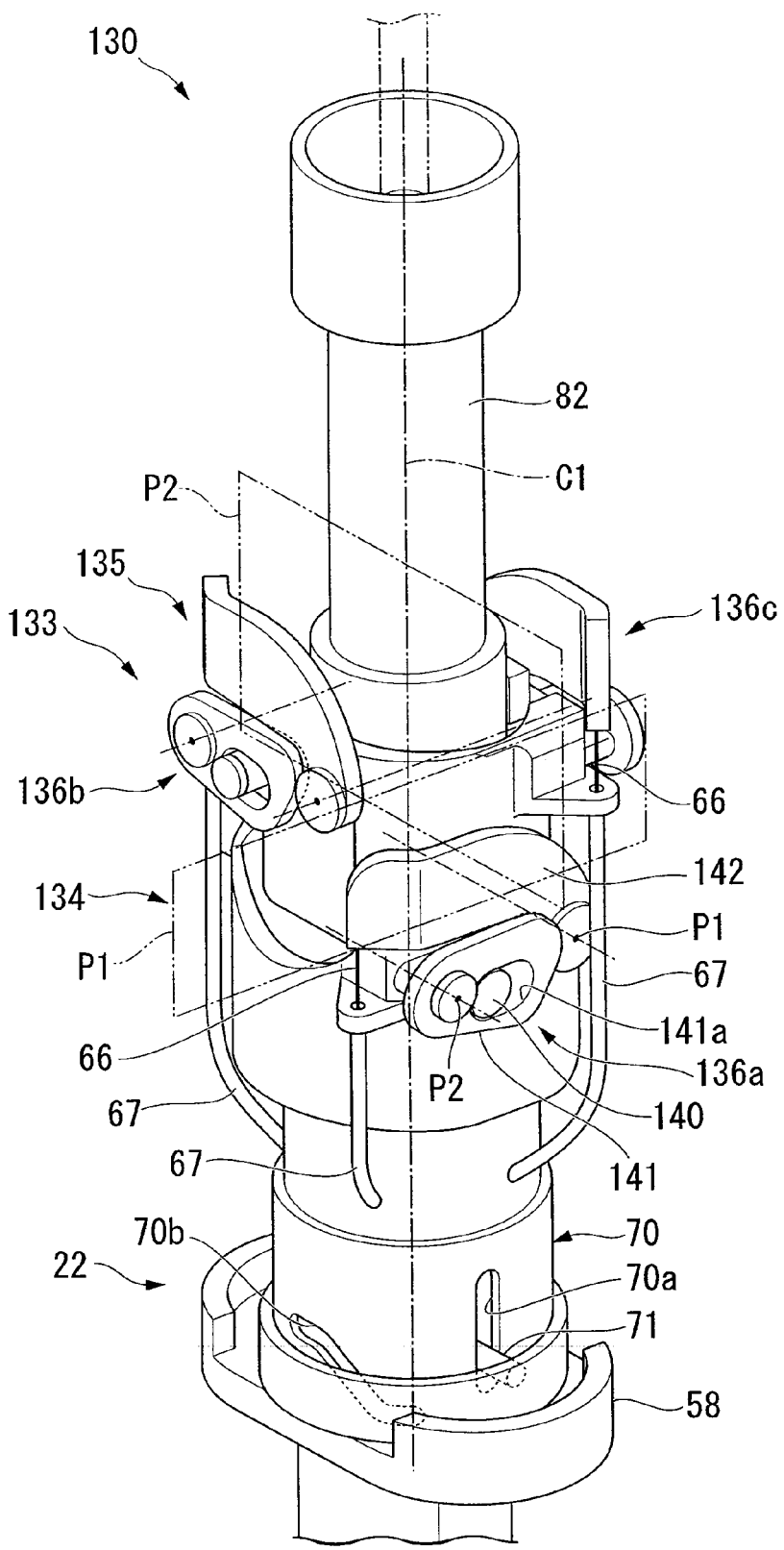
FIG. 17 is a perspective view showing a main part of the arm mechanism of the endoscope device according to a third embodiment of the present invention.

As shown in FIG. 17, an arm manipulating portion 133 of an arm mechanism 130 according to this embodiment includes a first oscillating portion 134 which oscillates on the plane P1 including the axis C1 relative to the body portion 22, a second oscillating portion 135 which is connected to the first oscillating portion 134 and oscillates on the plane P2 perpendicular to the plane P1 including the axis C1, and the cylindrical manipulation stick 82 which is fixed to the second oscillating portion 135.

Even in this embodiment, the arm portion manipulating wire 66 on the side opposite to the side where the manipulation stick 82 falls down is pulled, but four arm portion manipulating wires 66 are provided with four link mechanisms 136a to 136d having the same configuration in order to increase the pulling amount when the manipulation stick 82 is inclined by a predetermined angle.

The link mechanism 136a and the link mechanism 136d (not shown in figure) are included in the first oscillating portion 134. Then, the pair of link mechanisms 136a and 136d is disposed on both planes parallel to the panel P1 and away from the plane P1 by a predetermined distance so as to be symmetrical to each other with respect to the axis C1 of the body portion 22, and is operated on the respective planes so as to pull or push the base end of the arm portion manipulating wire 66. In addition, the link mechanism 136b and the link mechanism 136c are included in the second oscillating portion 135. Then, the pair of link mechanisms 136a and 136d is disposed on both planes parallel to the plane P2 and away from the plane P2 by a predetermined distance so as to be symmetrical to each other with respect to the axis C1 of the body portion 22, and is operated on the respective planes so as to pull or push the base end of the arm portion manipulating wire 66.

Figure 18:
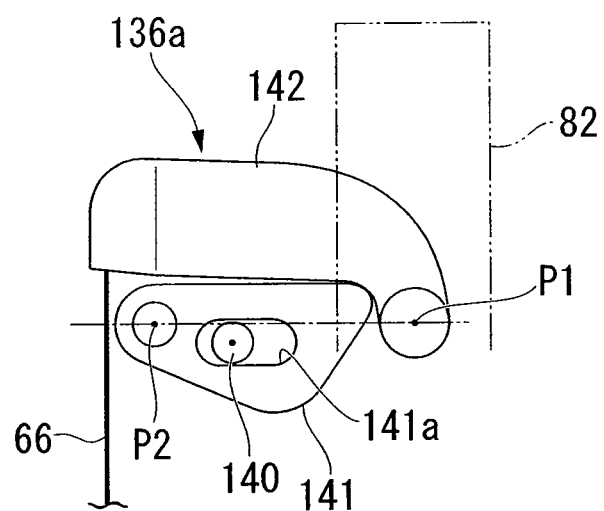
FIG. 18 is an explanatory diagram showing a link mechanism of the arm mechanism.

Next, the link mechanism 136a of the link mechanisms will be given as examples and schematically described. As shown in FIG. 18, the manipulation stick 82 is supported so as to be rotatable about the point P1, and a pin member 140 is fixed to the manipulation stick 82. One end of a first links 141 is supported so as to be rotatable about the point P2, and the inside thereof is provided with a slit 141a engaging with the pin member 140. One end of a second link 142 is supported so as to be rotatable about the point P1, and the other end thereof is fixed to the base end of the arm portion manipulating wire 66. Then, the other end of the first link 141 is locked to the vicinity of one end of the second link 142.

Figure 19:
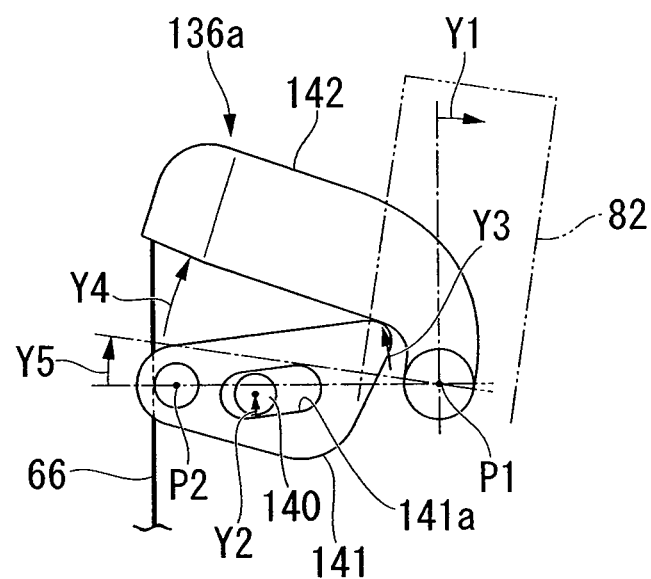
FIG. 19 is an explanatory diagram showing an operation of the link mechanism of the arm mechanism.

In the link mechanism 136a having the above-described configuration, as shown in FIG. 19, when the manipulation stick 82 is inclined in a direction depicted by the arrow Y1, the pin member 140 rotates about the point P1 so as to move inside the slit 141a in a direction depicted by the arrow Y2, thereby pushing up the other end of the first link 141 in a direction depicted by the arrow Y3. Then, the vicinity of one end of the second link 142 is locked to the other end of the first link 141, and the other end of the second link 142 is pushed up in a direction depicted by the arrow Y4 so as to pull the base end of the arm portion manipulating wire 66.

In addition, a case will be examined in which the manipulation stick 82 and the second link 142 are fixed to each other without the link mechanisms described so far and the manipulation stick 82 is supported so as to be rotatable about the point P1. In this case, since the second link 142 rotates about the point P1 by an angle corresponding to a degree that the manipulation stick 82 rotates about the point P1, the other end of the second link 142 is pushed up in a direction depicted by the arrow Y5, and the pushing-up amount is smaller than that when the link mechanism is used.

Likewise, in the link mechanisms 136a to 136d according to this embodiment, it is possible to increase the pulling amount of the arm portion manipulating wire 66 with respect to the inclined angle of the manipulation stick 82.

In addition, when the manipulation stick 82 is inclined in a direction opposite to the direction depicted by the arrow Y1 in the state shown in FIG. 18, the pin member 140 rotates about the point P1 so as to move inside the slit 141a in a direction opposite to the direction depicted by the arrow Y2, thereby pushing down the other end of the first link 141 in a direction opposite to the direction depicted by the arrow Y3. Then, the vicinity of one end of the second link 142 is pushed down by the other end of the first link 141, and the other end of the second link 142 is pushed down in a direction opposite to the direction depicted by the arrow Y4 so as to push in the base end of the arm portion manipulating wire 66.

In addition, in this embodiment, the link mechanisms 136a to 136d adopt a two-stage link structure, but the link structure may have several stages not less than one stage.

Fourth Embodiment

Hereinafter, another embodiment of the endoscope device according to the above-described embodiment will be described. Since the same reference numerals will be given to the same constituents as those of the above-described embodiment, the description thereof will be omitted, and only the different points will be described. In addition, for convenience of description, the partial shape in the drawings is omitted.

Figure 20:
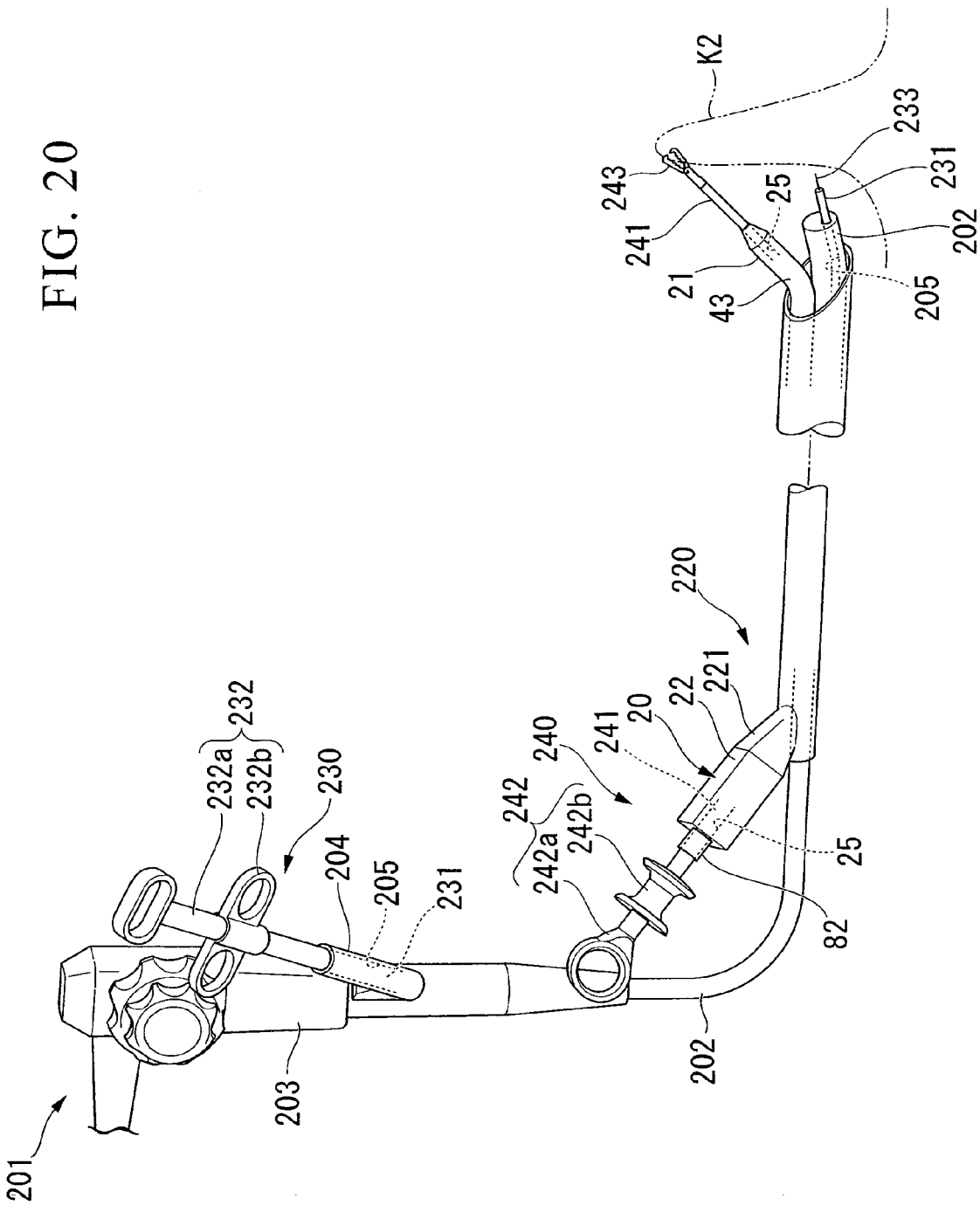
FIG. 20 is a perspective view showing the endoscope device according to a fourth embodiment of the present invention.

As shown in FIG. 20, an endoscope inserting portion 202 of an endoscope device 201 according to this embodiment is inserted through a lumen of an over tube (medical instrument) 220, and the front end of the endoscope inserting portion 202 protrudes forward from an opening formed in the front end of the over tube 220.

A lumen 205 is formed in a clamp opening 204 disposed in the endoscope manipulating portion 203 of the endoscope device 201, and the lumen 205 extends to a front end surface of the endoscope inserting portion 202 along the endoscope inserting portion 202.

For example, a treatment tool inserting portion 231 of a first treatment tool 230 as a high-frequency knife is inserted through the lumen 205, and the front end of the treatment tool inserting portion 231 protrudes forward from the front end of the endoscope inserting portion 202. The base end of the first treatment tool 230 is provided with a treatment tool manipulating portion 232, and the treatment tool manipulating portion 232 includes a manipulation portion body 232a which is attached to the base end of the treatment tool inserting portion 231 and a manipulation member 232b which is slidable on the manipulation portion body 232a in the longitudinal direction. In addition, when the manipulation member 232b is pushed into the manipulation portion body 232a, a high-frequency current flows from a high frequency generating device (not shown in figure) to a knife member 233 disposed in the front end of the treatment tool inserting portion 231.

Since the treatment tool manipulating portion 232 is disposed in the endoscope manipulating portion 203 of the endoscope device 201, one surgeon is capable of reciprocating and rotating the first treatment tool 230 relative to the clamp opening 204 of the endoscope manipulating portion 203, and manipulating the knife member 233. In addition, in the past, an assistant assisting the surgeon rotated and manipulated the treatment tool.

The base end of the over tube 220 is provided with a clamp opening 221, and the body portion 22 of the arm mechanism 20 of the above-described embodiment is attached to the clamp opening 221. In addition, the arm portion 21 of the arm mechanism 20 is inserted through the lumen of the over tube 220, and the front end of the arm portion 21 protrudes forward from the opening formed in the front end of the over tube 220. The front end of the over tube 220 may have a curve function. The arm portion 21 may be separably attached to the over tube 220. The arm mechanism 20 may not be provided with the second curve 42.

For example, a treatment tool inserting portion 241 of a second treatment tool 240 such as a griping clamp is inserted through the channel 25 formed in the arm mechanism 20. The base end of the second treatment tool 240 is provided with a treatment tool manipulating portion 242, and the treatment tool manipulating portion 242 includes a manipulation portion body 242a which is attached to the base end of the treatment tool inserting portion 241 and a manipulation member 242b which is slidable on the manipulation portion body 242a in the longitudinal direction. Then, when the manipulation member 242b is pushed into or pulled out from the manipulation portion body 242a, a gripping portion 243 disposed in the front end of the treatment tool inserting portion 241 is opened or closed.

In addition, the surgeon is capable of reciprocating or rotating the second treatment tool 240 relative to the arm mechanism 20, and manipulating the gripping portion 243.

The treatment using the endoscope device 201 and the over tube 220 having the above-described configuration is performed as follows.

First, in the inside of a patient's body, the treatment tool inserting portion 241 of the second treatment tool 240 protrudes from the front end of the arm portion 21, the treatment tool manipulating portion 242 of the second treatment tool 240 is manipulated so as to grip the target tissue K2 using the gripping portion 243, and then the manipulation stick 82 is oscillated through the treatment tool manipulating portion 242 so as to bend the first curve 43 and to pull the target tissue K2.

Next, the treatment tool inserting portion 231 of the first treatment tool 230 protrudes from the lumen 205 of the endoscope device 201, and the treatment tool manipulating portion 232 is manipulated so as to cut the target tissue K2.

In the endoscope device 201 having the above described configuration according to this embodiment, it is possible to observe an area on the side of the front end of the endoscope inserting portion by inserting the endoscope inserting portion 202 of the endoscope device 201 through the lumen of the over tube 220.

In addition, since the target tissue K2 is pulled and cut, it is possible to easily perform the cutting operation. Further, since it is possible to use two treatment tools, that is, the second treatment tool 240 for the pulling operation and the first treatment tool 230 for the cutting operation, it is possible to more easily perform the cutting operation.

In addition, as below, one surgeon can perform the above-described treatment. That is, for example, the surgeon performs a manipulation operation (an operation of twisting the endoscope inserting portion 202, an operation of manipulating an angle of the scope, and the like) the endoscope manipulating portion 203 using a left hand, and reciprocates the endoscope inserting portion 202 or manipulates the treatment tool manipulating portion 232 of the first treatment tool 230, the treatment tool manipulating portion 242 of the second treatment tool 240, and the arm mechanism 20 while holding the endoscope inserting portion 202 using a right hand.

Likewise, since the manipulation operation (a rotation operation or an opening/closing operation of the gripping portion in the gripping clamp) performed by an assistant can be performed by one surgeon, it is possible to solve the difficulty of cooperating with the assistant, and thus to perform the treatment by only a few surgeons.

Fifth Embodiment

Next, a fifth embodiment of the invention will be described. Since the same reference numerals will be given to the same constituents as those of the above-described embodiment, the description thereof will be omitted, and only the different points will be described.

Figure 21:
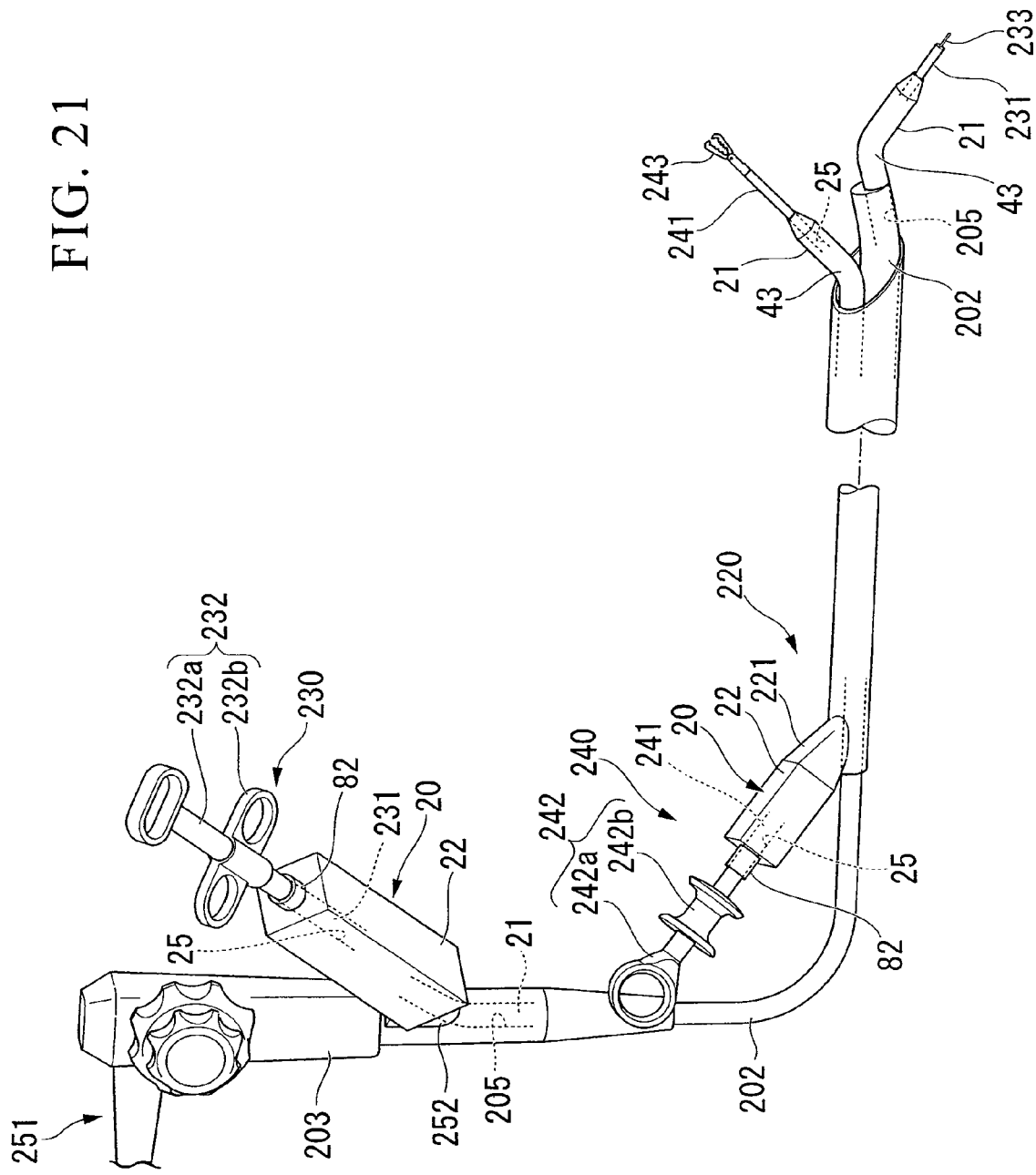
FIG. 21 is a perspective view showing the endoscope device according to a fifth embodiment of the present invention.

As shown in FIG. 21, in an endoscope device 251 according to this embodiment, a clamp opening 252 is provided instead of the clamp opening 204 of the endoscope device 201 according to the above-described embodiment, the arm portion 21 of the arm mechanism 20 is inserted through the lumen 205, and the body portion 22 is attached to the clamp opening 252. In addition, the front end of the arm portion 21 protrudes forward from the front end of the endoscope inserting portion 202.

The treatment tool inserting portion 231 of the first treatment tool 230 is inserted through the channel 25 formed in the arm mechanism 20, and the front end of the treatment tool inserting portion 231 protrudes forward from the front end of the arm portion 21. In addition, it is desirable that the arm mechanism 20 is provided with the second curve 42.

In the endoscope device 251 having the above-described configuration according to this embodiment, it is possible to exhibit the same advantage as that of the above-described embodiment. In addition, it is possible to curve the front end of the treatment tool inserting portion 231 of the first treatment tool 230 by using the arm mechanism 20 attached to the clamp opening 252.

In the past, since the treatment such as the cutting operation was performed by moving the treatment tool inserted through the endoscope together with the endoscope, the FOV of the endoscope moved during the treatment. In this embodiment, since the treatment is performed by curving the first curve 43 of the arm mechanism 20 attached to the clamp opening 252, it is possible to improve the operability of the surgeon by suppressing the movement of the FOV during the treatment.

So far, the embodiment has been described in which the first and second lumens 8 and 9 communicate with the passageways 37a formed in the side surface of the endoscope inserting portion 3 of the endoscope device, and two arm mechanisms are inserted through the lumens 8 and 9. However, when the positions of the passageways of the lumens are changed or the types of the treatment tools inserted through the lumens are changed, it is possible to perform various types of surgical techniques as described below.

Figure 22:
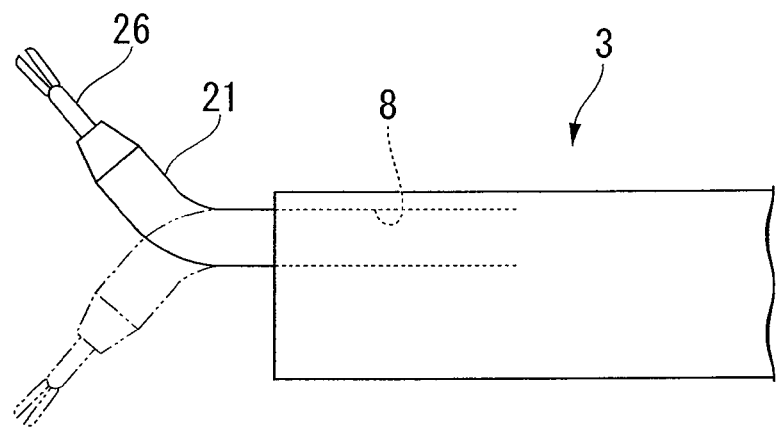
FIG. 22 is an explanatory diagram showing a main part of the endoscope device according to the present invention.
Figure 23:
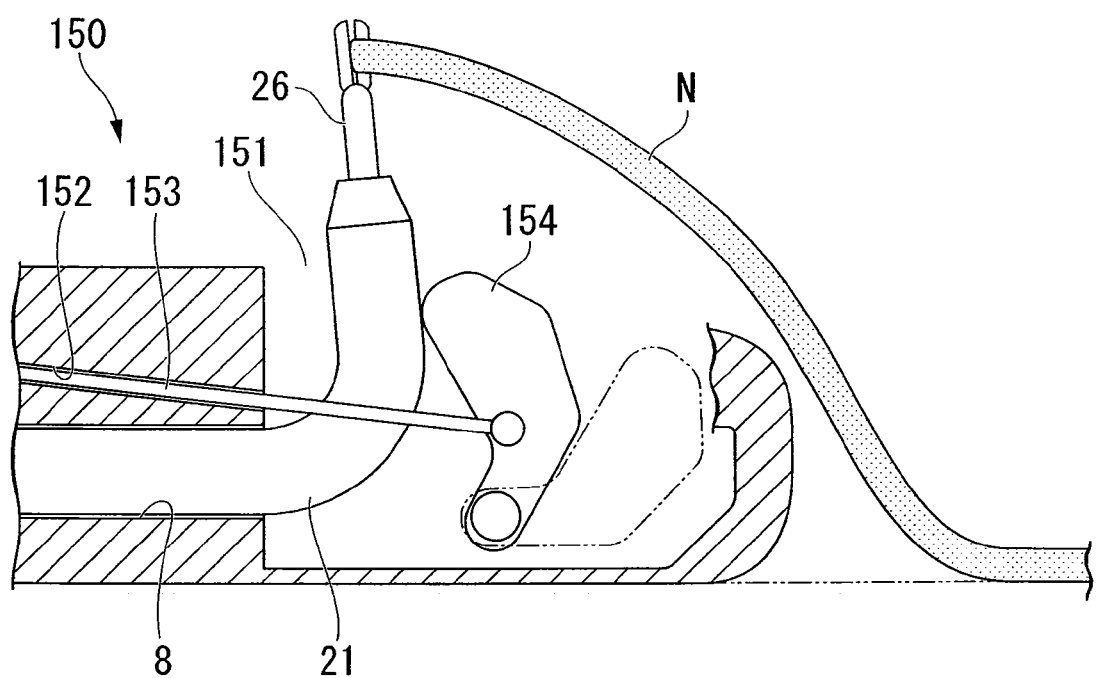
FIG. 23 is an explanatory diagram showing a main part of the endoscope device according to the present invention.

For example, as shown in FIG. 22, the first lumen 8 may be inserted through the passageway formed in the front end surface of the endoscope inserting portion 3, and the arm portion 21 without the second curve may be inserted through the first lumen 8. When the arm portion 21 is adapted to be bent just by the first curve, it is possible to shorten the rigid range which cannot be bent in the arm portion 21, and thus to perform the treatment in the inside of a comparatively narrow space such as a digestive canal.

In addition, the configuration shown in FIG. 22 may be used. That is, a passageway 151 is formed in a side surface of a front end of an endoscope inserting portion 150. Then, the passageway 151 is provided with a raising stand 154 rotated by an endoscope manipulating wire 153 inserted through a second lumen 152. With the above-described configuration, it is possible to bend the front end of the arm portion 21 inserted through the first lumen 8 by using the raising stand 154.

In addition, when the treatment tool 26 is configured as the gripping clamp, it is possible to elevate and pull a tissue such as a mucous membrane N by using the treatment tool 26. Further, when the high-frequency treatment tool is inserted through the arm portion 21 and is operated, it is possible to simply perform the treatment.

Figure 24:
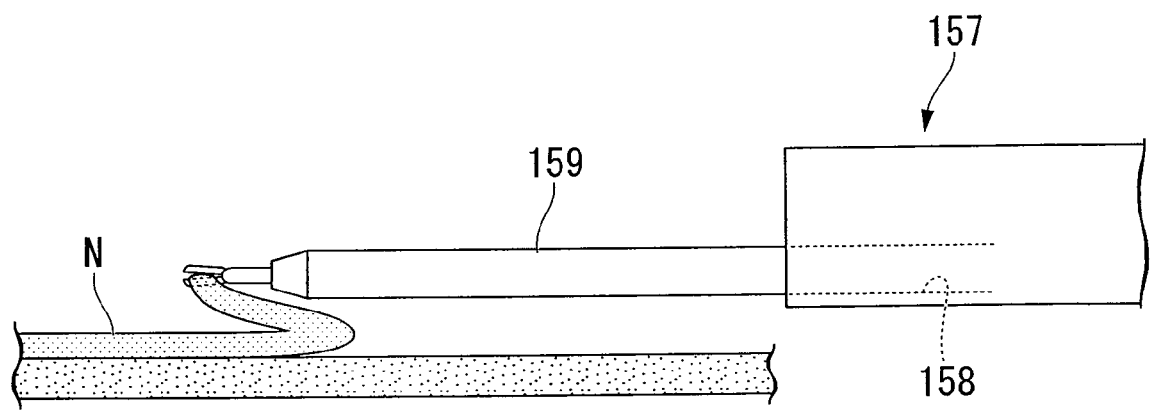
FIG. 24 is an explanatory diagram showing a main part of the endoscope device according to the present invention.

In addition, as shown in FIG. 24, an endoscope inserting portion 157 may be provided with a lumen 158 communicating with a passageway formed in the front end surface of the endoscope inserting portion, and a gripping clamp 159 may be inserted through the lumen so as to be movable in a reciprocating manner. It is possible to perform a treatment in such a manner that the mucous membrane N or the like is gripped by the gripping clamp 159 and is reciprocated. Further, the treatment may be performed by using a high-frequency treatment tool (not shown in figure) in the state shown in FIG. 24.

Figure 25:
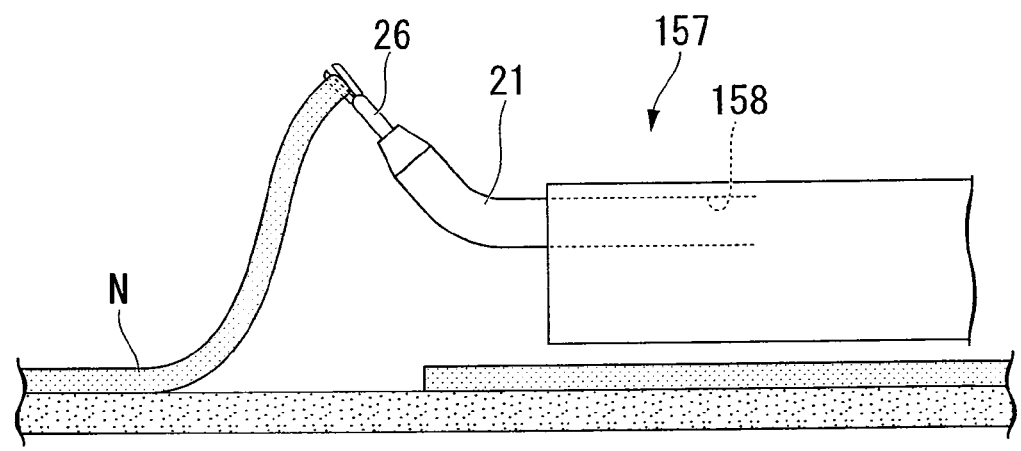
FIG. 25 is an explanatory diagram showing a main part of the endoscope device according to the present invention.
Figure 26:
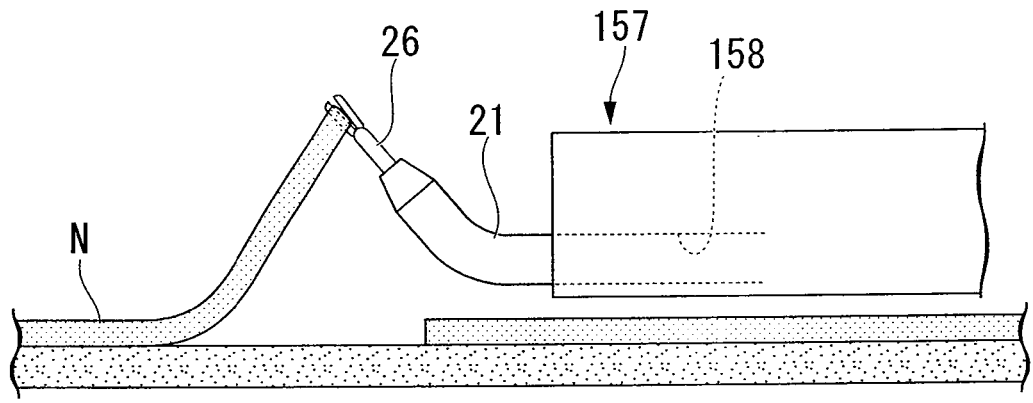
FIG. 26 is an explanatory diagram showing a main part of the endoscope device according to the present invention.

As shown in FIG. 25, in the case where the mucous membrane N or the like is elevated and pulled by the treatment tool 26 as the gripping clamp, it is desirable that the arm portion 21 is disposed so as to protrude forward from a position (upper position) of the endoscope inserting portion 157 away from the mucous membrane N. This is because the mucous membrane N or the like can be elevated and pulled up to a higher position compared with the case where the arm portion 21 protrudes forward from a position close to the mucous membrane N as shown in FIG. 26.

Figure 27:
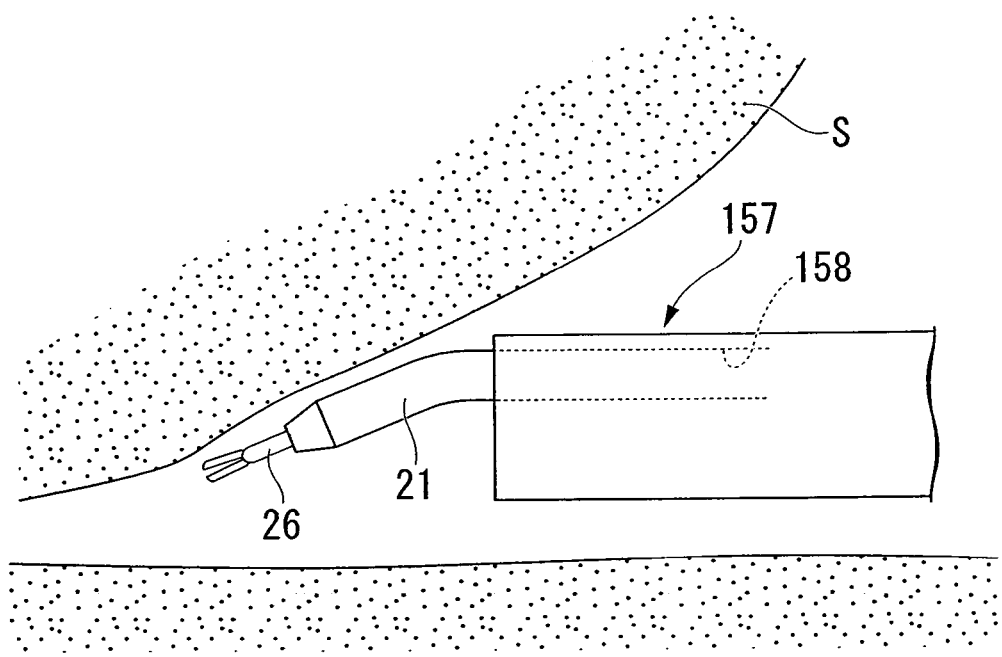
FIG. 27 is an explanatory diagram showing a main part of the endoscope device according to the present invention.

As shown in FIG. 27, in the case where the endoscope inserting portion 157 enters a lower portion of a tissue S, it is desirable that the arm portion 21 be disposed so as to protrude forward from the endoscope inserting portion 157 on the side of the tissue S (upper position). With the above-described disposed state, it is possible to ensure an FOV of a forward area or a treatment area by supporting the tissue S using the arm portion 21.

Figure 28:
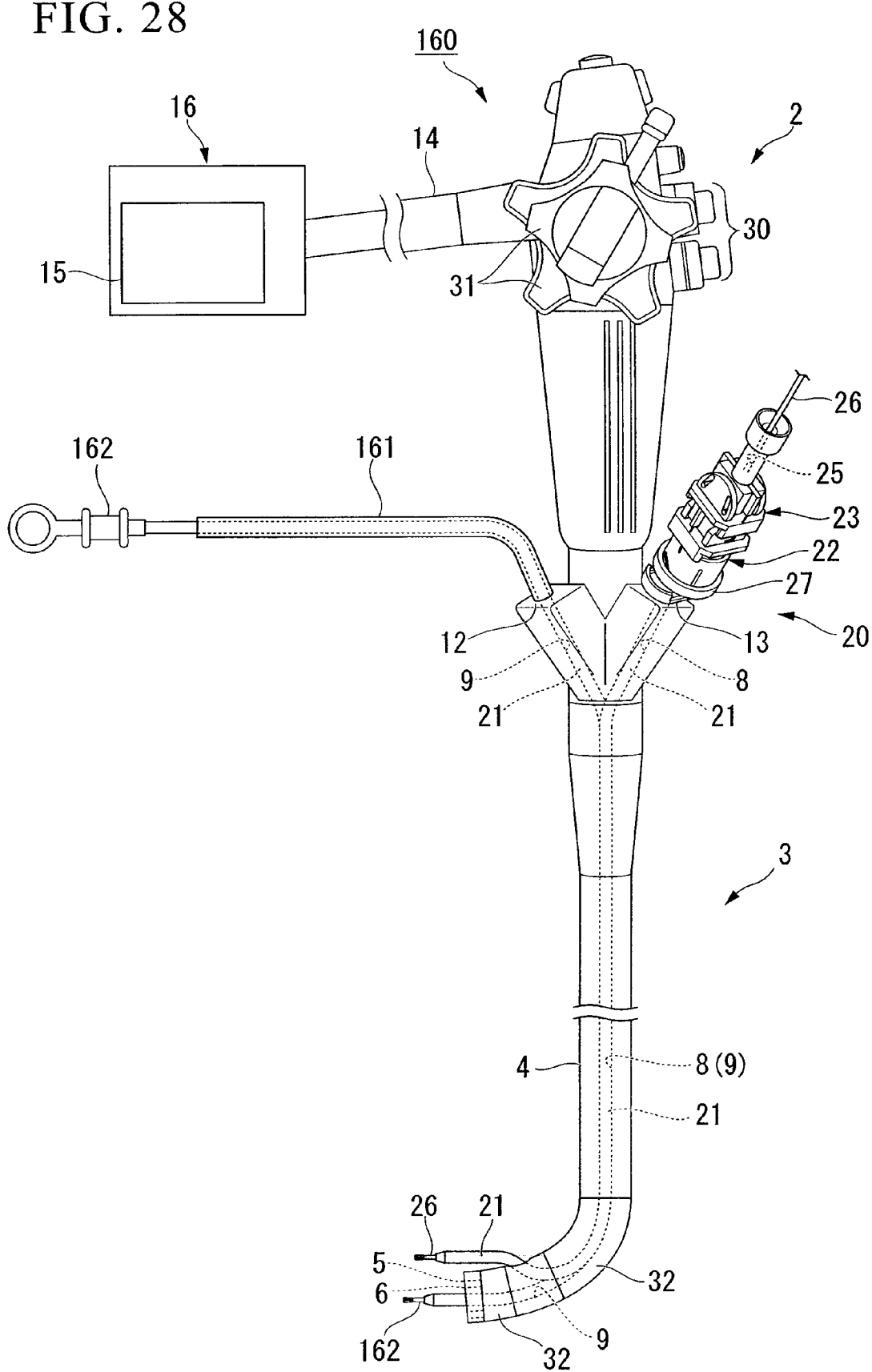
FIG. 28 is an explanatory diagram showing the endoscope device according to the present invention.

In the above-described embodiment, the case has been described in which one surgeon manipulates the endoscope device. However, as shown in FIG. 28, one end of a tube 161 may be attached to one clamp opening 12, and a treatment tool 162 for a general endoscope device may be inserted through the other end of the tube 161. With the above-described configuration, it is possible to adjust the protruding length of the treatment tool 162 from the front end of the endoscope inserting portion 3 based on the positional relationship between the other end of the tube 161 and the base end of the treatment tool 162. In addition, the manipulation operations may be shared in such a manner that the surgeon manipulates the endoscope manipulating portion 2 and the arm manipulating portion 23 and the assistant manipulates the treatment tool 162.

In addition, in FIG. 28, the arm mechanism 20 may be attached to the clamp opening 12 instead of the clamp opening 13, and the arm portion 21 may protrude forward from the front end of the endoscope inserting portion 3 through the second lumen 9.

Here, a difference in the characteristic of the treatment tools inserted through two lumens of the endoscope device and the existence of the assistant will be described with reference to FIG. 29.

In addition, in the case of the surgical technique performed without inserting the treatment tool through the lumen of the endoscope device, in many cases, the tissue or the like is gripped or pulled by the treatment tool manipulated by the surgeon's left hand, and the tissue or the like is separated by the treatment tool manipulated by the surgeon's right hand. For this reason, even in the case of the surgical technique performed by inserting two treatment tools through the lumens of the endoscope device, generally, it is desirable that the tissue or the like gripped and pulled by the treatment tool protruding forward from the front end of the endoscope device on the left side of the surgeon and the tissue or the like is separated by the treatment tool protruding forward from the front end on the right side thereof.

As in a pattern A shown in FIG. 29, in the case where the second curves are formed in both arm mechanisms, that is, the arm mechanism protruding forward from the left side of the front end of the endoscope inserting portion and the arm mechanism protruding forward from the right side of the front end, two treatment tools may be disposed in a triangular shape as shown in FIG. 7.

As in a pattern B, in the case where the second curve is not formed in any one of the arm mechanisms, that is, the arm mechanism protruding forward from the left side of the front end of the endoscope inserting portion and the arm mechanism protruding forward from the right side of the front end, it is not possible to dispose two treatment tools in a triangular shape. However, since it is possible to shorten the rigid range where the arm portion cannot be bent, it is possible to easily approach the treatment target even in the inside of a comparatively narrow space such as a digestive canal.

As in a pattern C, in the case where the arm mechanism provided with the second curve protrudes forward from the right side of the front end of the endoscope inserting portion and a general treatment tool such as a clamp protrudes forward from the left side of the front end, it is possible to perform the treatment such as a separation operation using the arm mechanism by gripping or elevating the tissue using the treatment tool. In addition, in the case where the arm mechanism provided with the second curve is disposed in the right side of the front end of the endoscope inserting portion and a clamp raising stand is disposed so as to bend the arm mechanism, it is possible to elevate and pull the tissue by inserting the treatment tool through the arm mechanism so as to bend the treatment tool by the clamp raising stand. In the case of the pattern C, the rigid range becomes long in the arm mechanism, but the arm mechanism may be disposed in a triangular shape.

As in a pattern D, in the case where the arm mechanism without the second curve being protruded forward from the right side of the front end of the endoscope manipulating portion and the general treatment tool such as the clamp protrudes forward from the left side of the front end, and in the case where the arm mechanism without the second curve being protruded forward from the right side of the front end of the endoscope manipulating portion and the clamp raising stand is disposed so as to bend the arm mechanism, it is possible to obtain the same advantage as that of the pattern C. Here, it is not possible to dispose the arm mechanism is a triangular shape, but it is possible to shorten the rigid range of the arm portion.

In addition, in the case of the right-handed surgeon, the combination shown in FIG. 29 is desirable. However, in the case of the left-handed surgeon, it is desirable to use the endoscope device in which the right and left in FIG. 29 are changed.

Further, a difference in the characteristic of the treatment using the treatment tool disposed in the front end of the endoscope manipulating portion and the existence of the assistant will be described with reference to FIG. 30.

As in a pattern A, in the case where the treatment tools protruding forward from both sides of the front end of the endoscope manipulating portion are the arm mechanisms, the surgeon alone performs the operations of reciprocating, opening/closing, and rotating two treatment tools inserted through the arm mechanisms. At this time, since all the manipulation operations are performed by the surgical surgeon, the surgeon alone can perform the surgical technique.

In patterns B to D, one of the treatment tools protruding forward from the front end of the endoscope manipulating portion is the arm mechanism, the other is the general clamp, and the tissue is turned over just by reciprocating the clamp. In this case, in the case where the assistant does not exist as in the pattern B, the surgeon performs the operations of reciprocating, opening/closing, and rotating the arm mechanism and the clamp. At this time, since all the manipulation operations are performed by the surgeon, the surgeon can perform the surgical technique alone.

In the case of the pattern C in which the assistant exists, the assistant performs the operations of opening/closing and rotating the clamp, and the surgeon performs the operation of reciprocating the clamp, since the manipulation is shared in the same manner as the general endoscope device, the surgeon and the assistant can have the same manipulation feeling as that of the general endoscope device. Then, in the case of the pattern D in which the assistant exists and the assistant performs the operations of reciprocating, opening/closing, and rotating the clamp, the surgeon can concentrate on the operations of manipulating the endoscope manipulating portion and one arm mechanism.

In patterns E to G, one arm mechanism protrudes forward from the front end of the endoscope manipulating portion, and the clamp raising stand is disposed so as to curve the arm mechanism. In the case where the assistant does not exist as in the pattern E, since the surgeon performs the operations of reciprocating, opening/closing, and rotating the arm mechanism and manipulating the clamp raising stand, the surgical alone can perform the surgical technique.

As in a pattern F, in the case where the assistant exists and the assistant performs the operations of opening/closing and rotating the treatment tool, since the manipulation is shared in the same manner as the general endoscope device, the surgeon and the assistant can have the same manipulation feeling as that of the general endoscope device. Then, in the case of the pattern G in which the assistant exists and the assistant performs the operations of reciprocating, opening/closing, and rotating the treatment tool, the surgeon can concentrate on the operations of manipulating the endoscope manipulating portion and the arm mechanism.

While preferred embodiments of the invention are as described and illustrated above, it should be understood that these are exemplary of the invention and are not to be considered as limiting. Additions, omissions, substitutions, and other modifications can be made without departing from the spirit or scope of the invention.

For example, in the above-described embodiments, the plane P1 where the manipulation stick 82 oscillates is perpendicular to the plane P2 where the second oscillating portion oscillates, but the planes P1 and P2 may intersect each other.

What is claimed is:

1. A manipulation mechanism comprising:
a manipulation reference plane which is perpendicular to an axis of the manipulation mechanism;
a first imaginary plane which includes the axis and which is perpendicular to the manipulation reference plane;
a second imaginary plane which includes the axis and which is perpendicular to the manipulation reference plane and the first imaginary plane;
a first oscillating portion which is configured to oscillate on the first imaginary plane;
a first guide member which is disposed on the first imaginary plane and which regulates an oscillating locus of the first oscillating portion;
a second oscillating portion which is configured to oscillate on the second imaginary plane;
a second guide member which is disposed on the second imaginary plane and which regulates an oscillating locus of the second oscillating portion; and
a manipulation stick which is fixed to the second oscillating portion and which is disposed so as to be capable of moving on the second imaginary plane,
wherein:
the first oscillating portion comprises:
a first force-transmitting-member attachment member configured so that a force transmitting member can be attached at both ends thereof;
a pair of first support members which is fixed with the first force-transmitting-member attachment member interposed there between; and
a force receiving member which is disposed in outer peripheral surfaces of base ends of the pair of first support members;
the second oscillating portion comprises:
a second force-transmitting-member attachment member configured so that a force transmitting member can be attached at both ends thereof; and
a pair of second support members which is fixed with the second force-transmitting-member attachment member interposed there between;
the first oscillating portion, the second oscillating portion and the manipulation stick are sequentially disposed on the axis;
the pair of first support members of the first oscillating portion is provided with first and second convex portions which are spaced from each other, which are disposed symmetrically to each other with respect to the axis, and which protrude in a direction orthogonal to the first imaginary plane;
the pair of second support members of the second oscillating portion is provided with first and second convex portions which are spaced from each other, which are disposed symmetrically to each other with respect to the axis, and which protrude in a direction orthogonal to the second imaginary plane;
the first guide member is provided with first and second groove portions which respectively guide, on the first imaginary plane, the first and second convex portions of the pair of first support members of the first oscillating portion;
the second guide member is provided with first and second groove portions which respectively guide, on the second imaginary plane, the first and second convex portions of the pair of second support members of the second oscillating portion; and
in each of the first and second guide members, the first and second groove portions are formed to be closer to each other in a direction away from the manipulation reference plane on one side of the manipulation reference plane from a point on the manipulation reference plane as a start point.

2. The manipulation mechanism according to claim 1, wherein, in each of the first and second guide members, the first groove portion is formed in a circular arc shape of which a center thereof is the start point in the second groove portion, and
wherein, in each of the first and second guide members, the second groove portion is formed in a circular arc shape of which a center thereof is the start point in the first groove portion.

3. The manipulation mechanism according to claim 1, wherein the first oscillating portion and the first guide member are formed to be symmetrical to each other with respect to the first imaginary plane, and
the second oscillating portion and the second guide member are formed to be symmetrical to each other with respect to the second imaginary plane.

4. The manipulation mechanism according to claim 1, wherein the second guide member is integrally formed with the first oscillating portion the oscillating body of the other pair.

5. A medical instrument comprising:
the manipulation mechanism according to claim 2;
an insertion portion which extends to the other side of the manipulation reference plane and has a base end attached to the manipulation mechanism;
a curve portion which is formed in the insertion portion so as to be bent;
a first force transmitting member which extends on the manipulation reference plane to the other side of the manipulation reference plane through the start point of the first groove portion of the first guide member and has a base end attached to the first force-transmitting-member attachment member of the first oscillating portion and a front end attached to a front end of the curve portion;
a second force transmitting member which extends on the manipulation reference toward the other side of the manipulation reference plane through the start point of the second groove portion of the first guide member and has a base end attached to the first force-transmitting-member attachment member of the first oscillating portion and a front end attached to a position different from the position where the front end of the first force transmitting member is attached to the front end of the curve portion;
a third force transmitting member which extends on the manipulation reference plane to the other side of the manipulation reference plane through the start point of the first groove portion of the second guide member and has a base end attached to the second force-transmitting-member attachment member of the second oscillating portion and a front end attached to a front end of the curve portion; and a fourth force transmitting member which extends on the manipulation reference toward the other side of the manipulation reference plane through the start point of the second groove portion of the second guide member and has a base end attached to the second force-transmitting-member attachment member of the second oscillating portion and a front end attached to a position different from the position where the front end of the third force transmitting member is attached to the front end of the curve portion.

6. The medical instrument according to claim 5, wherein tension is applied to each of the first and second force transmitting members.

7. The medical instrument according to claim 5, wherein the insertion portion is insertable through an operation channel formed in an endoscope.

8. The medical instrument according to claim 5, wherein a lumen is formed so as to allow an endoscope to be insertable there through.

9. The medical instrument according to claim 5, wherein the oscillating portion is provided with an oscillating-body-side channel, wherein the inserting portion is provided with an insertion-portion-side channel which is formed from the base end of the inserting portion to the front end thereof, and wherein the oscillating-body-side channel communicates with the insertion-portion-side channel.

10. The medical instrument according to claim 9,
wherein the oscillating portion is formed to extend in a predetermined direction, and
wherein the oscillating-body-side channel is formed from one end of the oscillating portion to the other end thereof.

11. The manipulation portion according to claim 10, wherein a length adjusting mechanism is disposed between the base end of the insertion portion and one end of the oscillating portion so as to adjust a distance between the insertion-portion-side channel and the oscillating-body-side channel and to communicate with the insertion-portion-side channel and the oscillating-body-side channel.

12. The medical instrument according to claim 5, wherein the insertion portion is attachable to or detachable from an operation channel of an endoscope.

13. The medical instrument according to claim 5, wherein the insertion portion is rotatable in a rotation direction about an axis thereof inside an operation channel of an endoscope.

14. The manipulation mechanism according to claim 2,
wherein the first oscillating portion and the first guide member are formed to be symmetrical to each other with respect to the first imaginary plane, and
the second oscillating portion and the second guide member are formed to be symmetrical to each other with respect to the second imaginary plane.

15. The manipulation mechanism according to claim 2,
wherein the second guide member is integrally formed with the first oscillating portion.

16. The manipulation mechanism according to claim 1,
wherein each of the first and second oscillating portions oscillates such that one of the first and second convex portions moves along the corresponding one of the first and second groove portions in a state where the other of the first and second convex portions stands at one end of the other of the first and second portions.

* * * * *